US006881560B2

(12) United States Patent
Peoples et al.

(10) Patent No.: US 6,881,560 B2
(45) Date of Patent: *Apr. 19, 2005

(54) POLYHYDROXYBUTYRATE POLYMERASE

(75) Inventors: Oliver P. Peoples, Arlington, MA (US); Anthony J. Sinskey, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 10/341,214

(22) Filed: Jan. 13, 2003

(65) Prior Publication Data

US 2005/0064565 A1 Mar. 24, 2005

Related U.S. Application Data

(63) Continuation of application No. 09/935,244, filed on Aug. 21, 2001, now Pat. No. 6,528,706, which is a continuation of application No. 08/922,007, filed on Sep. 2, 1997, now abandoned, which is a continuation of application No. 08/438,611, filed on May 10, 1995, now Pat. No. 5,663,063, which is a division of application No. 08/418,868, filed on Apr. 7, 1995, now Pat. No. 5,534,432, which is a continuation of application No. 08/234,721, filed on Apr. 28, 1994, now abandoned, which is a continuation of application No. 08/073,603, filed on Jun. 7, 1993, now abandoned, which is a continuation of application No. 07/944,881, filed on Sep. 14, 1992, now abandoned, which is a division of application No. 07/700,109, filed on May 8, 1991, now Pat. No. 5,245,023, which is a continuation of application No. 07/378,155, filed on Jul. 10, 1989, now abandoned, which is a continuation-in-part of application No. 07/067,695, filed on Jun. 29, 1987, now abandoned.

(51) Int. Cl.$^7$ ............................ C12P 7/62; C08G 63/00
(52) U.S. Cl. ....................................... 435/135; 528/361
(58) Field of Search ........................... 435/135; 528/361

(56) References Cited

U.S. PATENT DOCUMENTS

| | | |
|---|---|---|
| 3,275,610 A | 9/1966 | Coty |
| 4,477,654 A | 10/1984 | Holmes et al. |
| 5,229,279 A | 7/1993 | Peoples et al. |
| 5,245,023 A | 9/1993 | Peoples et al. |
| 5,250,430 A | 10/1993 | Peoples et al. |
| 5,512,669 A | 4/1996 | Peoples et al. |
| 5,534,432 A | 7/1996 | Peoples et al. |
| 5,661,026 A | 8/1997 | Peoples et al. |
| 5,663,063 A | 9/1997 | Peoples et al. |

FOREIGN PATENT DOCUMENTS

| | | |
|---|---|---|
| EP | 0 069 497 | 4/1987 |
| EP | 0 204 442 | 11/1991 |
| WO | WO 89/00202 | 1/1989 |
| WO | WO 92/19747 | 11/1992 |
| WO | WO 93/02187 | 2/1993 |
| WO | WO 93/02194 | 2/1993 |
| WO | WO 94/11519 | 5/1994 |
| WO | WO 94/23027 | 10/1994 |
| WO | WO 95/05472 | 2/1995 |

OTHER PUBLICATIONS

An, Binary Ti Vectors for Plant Transformation and Promoter Analysis, *Methods in Enzymology*, 153, 293–305 (1987).
Anderson, "Shotgun DNA Sequencing Using Cloned DNase 1–Generated Fragments," *Nucleic Acids*, 9, 3015–3026 (1981).
Anderson, et al., "Occurrence, Metabolism, Metabolic Role, and Industrial Uses of Bacterial Polyhydroxyalkanoates," *Microbiological Reviews*, 54(4), 450–472 (1990).
Bagdasarian, et al., "Activity of the Hybrid–trp–lac(tac) Promoter of *Escherichia coli* in *Pseudomonas putida*. Construction of Broad–Host–Range, Controlled–Expression Vectors," *Gene*, 26, 273–282 (1983).
Berg, et al., "The Prokaryotic Transposable Element Tn5," *Bio/Technology*, 1, 417–435 (1983).
Berk & Sharp, "Sizing and Mapping of Early Adenovirus mRNAs By Gel Electrophoresis of S1 Endonuclease–Digested," *Cell*, 12, 721–732 (1977).
Berndt & Schlegel, "Kinetics and Properties of β–Ketothiolase from *Clostridium pasteurianum*," *Arch. Microbiol.*, 103, 21–30 (1975).
Bighee, et al., "Monoclonal Antibodies Specific for the M– and N–Forms of Human Glycophorin A*," *Mol. Immunol.*, 20, 1353–1357 (1983).
Birnboim & Doly, "A Rapid Alkaline Extraction Procedure for Screening Recombinant Plasmid DNA," in *Nucleic Acids Res.*, 7, 1513–1523 (1979).
Bradford, "A Rapid and Senstive Method for the Quantitation of Microgram Quantities of Protein Utilizing the Principle of Protein–Dye Building," *Anal. Biochem.*, 72, 248–254 (1976).
Brandl, et al., "*Pseudomonas oleovorans* as a Source of Poly(β–Hydroxyalkanoates) for Potential Applications as Biodegradable Polyesters," *App. Environ. Microbiol.*, 54, 1977–1982 (1988).

(Continued)

*Primary Examiner*—Charles L. Patterson, Jr.
(74) *Attorney, Agent, or Firm*—Pabst Patent Group LLP

(57) ABSTRACT

A method for controlling and modifying biopolymer synthesis by manipulation of the genetics and enzymology of synthesis of polyhydroxybutyrate (PHB) and polyhydroxyalkanoate (PHA) polyesters at the molecular level in procaryotic and eukaryotic cells, especially plants. Examples demonstrate the isolation, characterization, and expression of the genes involved in the production of PHB and PHA polymers. Genes encoding the enzymes in the PHB and PHA synthetic pathway (beta-ketothiolase, acetoacetyl-CoA reductase and PHB polymerise or PHA polymerase) from *Zooloea ramigera* strain I-16-M, *Alcaligenes eutrophus*, *Nocardia salmonicolur*, and *Psuedomnas olevarans* were identified or isolated and expressed in a non-PHB producing organism, *E. coli*. Specific modifications to the polymers include variation in the chain length of the polymers and incorporation of different monomers into the polymers to produce co-polymers with different physical properties.

13 Claims, 18 Drawing Sheets

OTHER PUBLICATIONS

Burnette, "'Wester Blotting': Electrophoretic Transfer of Proteins from Sodium Dodecyl Sulfate–Polyacrylamide Gets to Unmodified Nitrocellulose and Radiographic Detection with Antibody and Radioiodinated Protein A," *Anal. Biochem.*, 112, 195–203 (1981).

Cashmore, "Nuclear Genes Encoding the Small Subunit of Ribulose–1,5–Bisphosphate Carboxylase," 29–38.

Comai, et al., "Expression in Plants of a Mutant *aroA* Gene from *Salmonella typhimurium* confers Tolerance to Glyphosate," *Nature*, 317, 741–744 (1985).

Davis, et al., "Biosynthetic Thiolase from *Zoogloea ramigera*," *J. Biol. Chem.*, 262, 82–89 (1987).

De Block, et al., "Engineering Herbicide Reistance in Plants by Expression of a Detoxifying Enzyme," 2513–2518 (1987).

De Smet, et al., "Characterization of Intracellular Inclusions Formed by *Pseudomonas oleovorans* During Growth on Octane," *J. Bacteriol.*, 154(2), 870–878 (1983).

Ditta, et al., "Broad Host Range DNA Cloning System for Gram–Negative Bacteria: Construction of a Gene Bank of Rhiozobium Meliloti," *Proc. Natl. Acad. Sci. USA*, 77(12), 7347–7351 (1980).

Easson, et al., "Isolation and *Zoogloea ramigera* I–16–M Exopolysaachride Biosynthetic Genes and Evidence for Instability Within this Region," *J. Bacteriol.*, 169, 4518–4524 (1987).

Everett, et al., "Genetic Engineering of Sunflower (*Helinathus annuus* L.)," *Bio/Technology*, 5, 1201–1204 (1987).

Firoozobady, et al., "Transformation of Cotton (*Gossypium hirsutum* L.) by *Agrobacterium tumefaciens* and Regeneraton of Transgenic Plants," *Plant Molecular Biology*, 10, 105–116 (1987).

Fischhoff, et al., "Insect Tolerant Transgenic Tomato Plants," *Bio/Technology*, 5, 807–813 (1987).

Friedman, et al., "Construction of a Broad Host Range Cosmid CloningVector and its Use in the Genetic Analysis of Rhizobium Mutants," *Gene*, 18, 289–296 (1982).

Fromm, et al., Electroporation of DNA and RNA into Plant Protoplasts, *Methods of Enzymology*, 153, 351–366 (1987).

Fukui, et al., "Enzymatic Synthesis of Poly–β–Hydroxybutyrate in *Zoogloea ramigera*," *Arch. Microbiol.*, 110, 149–156 (1976).

Fukui, et al., "Purification and Characterization of NAD-P–Linked Acetoacetyl–CoA Reductase from *Zoogloea ramigera* I–16–M," *Biochem. Biophys. Acta*, 917, 365–371 (1987).

Gill, et al., "Overproduction and Assay of *Pseudomonas aeruginosa* Phosphomannose Isomerase," *J. Bact.*, 167, 611–617 (1986).

Griebel & Merrick, "Metabolism of Poly–β–Hydroxybutyrate: Effect of Mile Alkaline Extraction on Native Poly–β–Hydroxybutyrate Granules," *J. Bacteriol.*, 108, 782–789 (1971).

*Handbook of Plant Cell Culture*, vol. 4, edited by D.A. Evans, W.R. Sharp, and P.V. Ammirate (Macmillan Publishing Co., NY 1986) (contents only).

Haywood, et al., "The Importance of PHB–Synthese Substrate Specificity in Polyhydroxyalkaneate synthesis by *Alcaligenes eutrophus*," *Chemical Abstracts*, 110(15) p. 404, Abstract 131921p (1989).

Hiatt, et al., "Production of Antibodies in Transgenic Plants," *Nature*, 342, 76–78 (1989).

Hinchee, et al., "Production of Transgenic Soybean Plants Using Agrobacterium–Mediated DNA Transfer," *Bio/Technology*, 915–922 (1988).

Hinnenbusch, et al., "Repeated DNA Sequences Upstream from HISI Also Occur at Several Other Co–Regulated Genes in *Saccharomyces cerevisiae*\*," *J. Biol. Chem.*, 258, 5238–5247 (1983).

Hoekema, et al., "The Genetic Engineering of Two Commercial Potato Cultivars for Resistance to Potato Virus X," *Bio/Technology*, 7, 273–278 (1989).

Hohn & Murray, "Packagin Recombinant DNA Molecules into Bacteriophage Particles in Vitro," *Proc. Natl. Acad. Sci., USA*, 74, 3259–3263 (1977).

Hooykaas, et al., "Detection of Monocot Transformation via *Agrabacterium tumefaciens*," *Methods in Enzymology*, 153, 305–313 (1987).

Horsch, et al., "Inheritance of Functional Foreign Genes in Plants," *Science*, 223, 496–498 (1983).

Ish–Horowicz & Burke, "Rapid and Efficient Cosmid Cloning," *Nucleic Acids Res.*, 9, 2989–2998 (1981).

Kleckner, et al., "Genetic Engineering in Vivio Using Translocatable Drug–Reistance Elements," *J. Mol. Biol.*, 116, 125–159 (1977).

Laemmli, "Cleavage of Structural Proteins During the Assembly of the Head of Bacteriophage T4," *Nature*, 222, 680–685 (1970).

Lageveen, et al., "Formation of Polyesters by *Pseudomonas oleovorans*: Effect of Substrates on Formation and Composition of Poly–(R)–3–Hydroxyalkanoates and Poly–(R)–3–Hydroxyalkenoates," *Appl. Environ. Microbiol.*, 54, 2924–2932 (1988).

Langridge, et al., "Uptake of DNA and RNA into Cells Mediated by Electroporation," *Methods in Enzymology*, 153, 336–350 (1987).

Law & Slepecky, "Assay of Poly–β–Hydroxybutyric Acid," *J. Bacteriol*, 82, 33–36 (1961).

Lehrach, et al., "RNA Molecular Weight Determinations by Gel Electrophoresis Under Denaturing Conditions, a Critical Reexamination," *Biochemistry*, 16, 4743–4751 (1977).

Lichtenstein & Fuller, "Vectors for the Genetic Engineering of Plants," *Genetic Engineering*, ed. P.W.J. Rigby, vol. 6, 104–183 (Academic Press Ltd. 1987).

Lloyd, et al., "Transformation of *Arabidopsis thaliana* with *Agrobacterium tumefaciens*," *Science*, 234, 464–466 (1986).

Maniatis, et al., *Molecular Cloning: A Laboratory Manual*, (Cold Spring Harbor Laboratory, Cold Spring Harbor, NY 1982) (contents only).

McCabe, et al., "Stable Transformation of Soybean (*Glycine Max*) by Particle Acceleration," *Bio/Technology*, 6, 923–926 (1988).

McMaster & Carmichael, "Analysis of Single– and Double–Stranded Nucleic Acids on Polyacrylamide and Agagrose Gels by Using Glyoxal and Acridine Orange," *Proc. Natl. Acad. Sci. USA*, 74, 4835–4838 (1977).

Mermod, et al., "Vector for Regulated Expression of Cloned Genes in a Wide Range of Gram–Negative Bacteria," *J. Bacteriol.*, 167, 447–454 (1986).

Mills & Kramer, "Structure–independent Nucleotide Sequence Analysis," *Proc. Natl. Acad. Sci. USA*, 76, 2232–2235 (1979).

Nishimura, et al., "Purification and Properties of β–Ketothiolase from *Zoogloea ramigera*," *Arch. Microbiol.*, 116, 21–27 (1978).

Oeding & Schlegel, "β–Ketothiolase from *Hydrogenomonas eutrophoa* H16 and its Signifigance in the Regulation of Poly–β–Hydroxybutyrate Metabolism," *Biochem. J.*, 134, 239–248 (1973).

Peoples, et al., "Biosynthetic Thiolase from Zoogloea Ramigera," *J. Biol. Chem.*, 262(1), 97–102 (1987).

Peoples, et al., "Poly–β–hydroxy–butyrate (PHB) Biosenthesis in *Alcaligenes eutrophus* H16," *The Journal of Biological Chemistry*, 264(26), 15298–15303 (1989).

Peoples, et al, "Poly–β–hydroxy–butyrate Biosenthesis in *Alcaligenes eutophus* H16," *The Journal of Biological Chemistry*, 264(26), 15293–15297 (1989).

Peoples, et al., "Polyhydroxybutyrate (PHB): A Model System for Biopolymer Engineering," *Novel Biodegradable Microbial Polymers*, 186, 191–201 (1990).

Ploux, et al., "The NADPH–Linked Aceto–acetyl–CoA Reductase from *Zoogloea ramigera*," *Eur. J. Biochem.*, 174, 177–182 (1988).

Poirier, et al., "Progress Toward Biologically Produced Biodegradable Thermoplastics," *Adv. Mater.*, 5(1), 30–37 (1993).

Pool, "In Search of the Plastic Potato," *Science*, 24, 1187–1189 (1989).

Pua, et al., "Transgenic Plants of *Brassica napus* L.," *Bio/Technology*, 5, 815–817 (1987).

R&D Magazine, Feb., 1991, pp. 56–57.

Ramos, et al., "Broad–host Range Expression Vectors Containing Manipulated meta–cleavage Pathway Regulatory Elements of the TOL Plasmid," *FEBS LETTERS*, 226, 241–246 (1986).

Rhodes, et al., "Genetically Transformed Maize Protoplasts," *Science*, 240, 204–207 (1987).

Rigby, et al., "Labeling Deoxyribonucleic Acid to High Specific Activity in Vitro by Nick Translation with DNA Polymerase I," *J. Mol. Biol.*, 113, 237–251 (1977).

Rogers, et al., "Improved Vectors for Plant Transformation: Expression Cassette Vectors and New Selectable Markers," *Methods in Enzymology*, 153, 253–277 (1987).

Saito, et al., "An NADP–Linked Acetoacetyl CoA Reductase," *Arch. Microbiol.*, 114, 211–217 (1977).

Sancar, et al., "Simple Method for Identification of Plasmid–Coded Proteins," *J. Bacteriol.*, 137, 692–693 (1979).

Kikucli, et al., "Circularization of Linear Viroid RNA via 2'–Phosphomonoester, 3', 5'–Phosphodiester Bonds by a Novel Type of RNA Ligase from Wheat Germ and Chlamydomonas," *Nucleic Acids Res.*, 10, 7521–7529 (1982).

Sanger, et al., "DNA Sequencing with Chain–Terminating Inhibitors," *Proc. Natl. Acad. Sci. USA*, 74, 5463–5467 (1977).

Schlegel & Oeding, *Radiation and Radioisotopes for Industrial Microorganisms*, International Atomic Energy Agency, Vienna, 223–231 (1971).

Schlegel, et al., "The Isolation of Mutants not Accumulating Poly–β–Hydroxybutyric Acid," *Arch. Microbiol.*, 71, 283–294 (1970).

Schreier, et al., "The Use of Nuclear–Encoded Sequences to Direct the Light–Regulated Synthesis and Transport of a Foreign Protein into Plant Chloroplasts," *EMBO Journal*, 4(1) 25–32 (1985).

Schubert , et al., "Cloning of the Alcaligenes eutrophus Genes for Synthesis of Poly–β–hydroxybutyric Acid (PHB) and Synthesis of PHB in *Escherichia coli*," *J. Bacteriol*, 170(12), 5837–5847 (1988).

Senior & Dawes, "The Regulation of Poly–β–Hydroxybutyrate Metabolism in *Azotobacter beijerinckii*," *Biochem. J.*, 134, 224–238 (1973).

Shillito, et al., "Direct Gene Transfer to Protoplasts of Dicotyledonous and Monocotyledonous Plants by a Number of Methods, Including Electroporation," *Methods in Enzymology*, 153, 313–337 (1987).

Simon, "High Frequency Mobilization of Gram–Negative Bacterial Replicons by the In Vitro Constructed Tn5–Mob Transposon," *Mol. Gen. Genet.*, 196, 413–420 (1984).

Simon, et al., "A Broad Host Range Mobilization System for In Vivo Genetic Engineering: Transposon Mutagenesis in Gram Negative Bacteria," *Bio/Technology*, 1(9), 784–791 (1983).

Simon, et al., *Molecular Genetics of the Bacteria–Plant Interaction*, A. Pühler, ed. (Spring–Verlag, NY, 1983) (contents only).

Slater, et al., "Cloning and Expression in *Excherichia coli* of the *Alcaligenes eutrophus* H16 Poly–β–Hydroxybutyrate Biosynthetic Pathway," *J. Bacteriol*, 170(10), 4431–4436 (1988).

Smith & Summers, "The Bidirectional Transfer of DNA and RNA to Nitrocellulose or Diazobenzyloxymethyl–Paper," *Anal. Biochem.*, 109, 123–129 (1980).

Southern, "Detection of Specific Sequences Among DNA Fragments Separated by Gel Electrophoresis," *J. Mol. Biol.*, 98, 503–517 (1975).

Spratt, et al., "Cloning, Mapping and Expression of Genes Involved in the Fatty Acid–Degradative Multienzume Complex of *Escherichia coli*," *J. Bacteriol*, 158(2) 535–542 (1984).

Stalker, et al., "Herbicide Resistance in Transgenic Plants Expressing a Bacterial Detoxification Gene," *Science*, 242, 419–423 (1988).

Steinbuchel, et al., "Molecular Basis for Biosynthesis and Accumulation of Polyhydroxyalkanoic Acids in Bacteria," *FEMS Microbiology Reviews*, 103, 217–230 (1992).

Streber, et al., "Transgenic Tobacco Plants Expressing a Bacterial Detoxifying Enzyme are Resistant to 2,4–D," *Bio/Technology*, 7, 811–816 (1989).

Suggs, et al., "Use of Synthetic Oligonucleotides as Hybridization Probes: Isolation of Cloned cDNA Sequences for Human–β–Microglobulin," *Proc. Natl.. Acad. Sci., USA*, 76(11), 6613–6617 (1981).

Teeri, et al., "Gene Fusions to tacZ Reveal New Expression Patterns of Chimeric Genes in Transgenic Plants," *EMBO Journal*, 8(2), 343–349 (1989).

Thomas, "Hybridization of Denatured RNA and Small DNA Fragments Transferred to Nitrocellulose," *Proc. Natl. Acad. Sci. USA*, 77:5201–5205 (1980).

Tomita, et al., "Bacterial Metabolism of Poly–beta–hydroxybutyrate," *Greenbock–Lilly Symposium in Honor of Dr. H.A. Hardyh*, Jun. 9–11, 1982, pp. 1–14.

Umbeck, et al., "Genetically Transformed Cotton (*Gossypium hirsutum* L.) Plants," *Bio/Technology*, 5, 263–266 (1987).

Yanisch–Perron, et al., "Improved M13 Phage Cloning Vectors and Host Strains: Nucleotide Sequences of the M13mp18 and pUC19 Vectors," *Gene*, 33, 103–109 (1985).

Young, & Davis, "Yeast RNA Polymerase II Genes: Isolation with Antibody Probes," *Science*, 222, 778–782 (1983).

Young, et al., "Efficient Isolation of Genes by Using Antibody Probes," *Proc. Natl. Acad. Sci., USA*, 80, 1194–1198 (1983).

```
Sal
  1 GTCGACTCAAAAAATCAGTCTAGGGAGTGAGCGACATGAGCAGGTAGCATTCGTAACGGGGGATCGCGGGCCATCCCCGCAGCCATTCGATT      96
                              MetSerArgValAlaLeuValThrGlyGlySerArgGlyIleGlyAlaAlaIleSerIle

97 GGGCTGAAGGCCGGGATACAAGGTGGCTGCCAGTCGATGCGGCCAATGACGACCCCTTCAAGGCCGAAACGGGCATCGCCGTCTAC           192
    AlaLeuLysAlaAlaGlyTyrLysValAlaAlaSerTyrAlaGlyAsnAspAspAlaAlaLysProPheLysAlaGluThrGlyIleAlaValTyr

193 AAGTGGGACGTGTCGAGCTACGAGGCCTGGGTCGAGGTGAGCCCCAAGGTGAGAGCCCATCGGCCCGATTGACGTTCTCGTCAACAATGCCGGC   288
    LysTrpAspValSerSerTyrGluAlaCysValGluGlyIleAlaLysValGluAlaAspLeuGlyProIleAspValLeuValAsnAsnAlaGly

289 ATCACCAAGGACCCCATGTTCCACAAGATGACCCGGTCATCAACAACCCAGTGAATGGCCGTCTCTTCAACATGACCCATCCG              384
    IleThrLysAspAlaMetPheHisLysMetThrProAspGlnTrpAsnAlaValIleAsnThrAsnLeuThrGlyLeuPheAsnMetThrHisPro

385 GTCGTGTCCGCATGCGGCACCCAGCTTCGGCCAGCATCGTCAACATCTCCTCGATCAACGGCCAGAAGGGCCAGATGGGTCAGGCGAACTATTCC   480
    ValTrpSerGlyMetArgAspArgSerPheGlyArgIleValAsnIleSerSerIleAsnGlyGlnLysGlyGlnMetGlyGlnAlaAsnTyrSer

481 GCCCCCAAGGCCGGGACCTCGGCTTCACCAAGGCGCTTCACCAAGGCGATCAAGGGCATCACCGTCAACGCCATCTGCCCCGGCTATATC       576
    AlaAlaLysAlaGlyAspLeuGlyPheThrLysAlaLeuAlaGlnGluGlyAlaLysGlyIleThrValAsnAlaIleCysProGlyTyrIle

577 GGTACGGAAATGGTGCCGCCATTCGGGAAAAGTCCTGAACGAGCGGATCATCCGGATCATCCCGATCATCCCGATCCCGAGCCGGAGATC       672
    GlyThrGluMetValArgAlaIleArgGluLysValLeuAsnGluArgIleIleProGlnIleIleProValGlyArgLeuGluProAspGluIle

673 GCCCGCATCGTCTTCCTCCGCCTCGGACAGGGCCGGCTTCATCACCGGCTTCATCACCGGCTTCGACCATCTCGGCAACGGCCAGTTCTTCGTCTGATACCGG   768
    AlaArgIleValPheLeuAlaSerThrIleSerThrIleSerAlaAsnGlyGlyGlnPhePheVal*
```

```
 769  CCACACGAAACGGAACGGGGGAACGGGCCTTCGGGGCGCCCTTTTCATGTGTATGCTGTCGAAAGGAGAGCCCGATGAAACAGGAAACAGGAAAAGCTGATGAGG   864
 865  CGGCGATTGCCGAGGCGCTGGCATCCCTGGAAGGATGGATTCGCTCGGCTGACCGGCCCATCGCCCATCGAGAAGCCTACACGTTCAAGAGCTTCCGCG        960
 961  AGGCGTTCGGCTTCATGACCGGCGAGGGCGCTGGCGAGAATTCAACCACCATCCGGAATGTTCAAGCTCTACAATCCGTCGACGTCGCGC                1056
1057  TGACCAACCACCGATGCCGGGGCCGCTGACCGAGCTGAAGCTGGACTTCAAGCTGGACTTCAAGCTGGGGGGCCCTTTCGCACGAAGACTTGAAGCG        1152
1153  GGGTGAACGCATTCCCATATGATCAGCCCGGACTGTTCCGGCGCTGCACCCGAGGGAGGCCCTTGAATGGACGATGTGAAGATGGGCGAGATTCT          1248
1249  GCTGCCCGGGACAAGGACGAGCAGGAGCGTCAGGAAAAGCCCGGTTCTGAGGGCGCGTTCTGCGCGCTCTCAAGGCGCGATGGGCCAGGTTCCCTT          1344
                                                           Sma
1345  CGCCCCGGGATCTCGCGGTCGCTACTATTGCGCCTCGATCCCCACACGCCCGGGGGCGGGGGCCATCCTTGCCGTCGCCCTTCGGGGATCCGGGGCCA       1440
                                               Sma
1441  GCTGCCGCTGACCGCGGCATACCCGGATTCTCTTCGCGCTCGTCGTTCCCGCGTCGCGGACCTTCGGTTGAGCGGGCCGGCCAATCGGGTC             1536
1537  TGTTCGGACGACCATTACGCGCCATTAGGCATCTGTGCCATTCATCTCGACGGGTTCATCTCAACCGGTTGCGGCACGCCCGCTTTCACGAAAGGCTGCG   1632
1633  AAATTCTTGCCCTATTCCTTGTGCCGGACAGGGTTCGTCCCGTGCGCCGGAAGACCTCGGCAAAATGCGTGCGTTGTTGACGGTTTGGTAACCTGAATTAAGTCAAATA 1728
1729  GCGGACTTCGACACGGTTTCGTCATCAAGCCATGCCGGGCCAATCACTGGCAAGACAACCGGCAGGAAAACATGTTC                           1824
1825  AATCAAATCGTCATCAAGCCACTCGGCCCTGCCCAGGCGTTGCCTGGACCGGCGTTGCCTGGACCGGCAAAGCGCCGACGGCATTCAGCAGTTCAATGCCTGG 1920
1921  GTAAGAAAGCTCGCAACCGGCACTCGCCCTCGCCCTCGCTGCGGGCAAGGTCTGCCTACGTGCTCGTCGTCCGTGCGAAGGAAAGACGCCGCCCGGG       2016
2017  GGGGCCCTATTCCTATCAGGGCGAATGGGCGGCAAGGTCTGCCTACGTGCTCGTCGTCCGTGCGAAGGAAAGACGCCGCCCGGG      2094
                                                                                            Sma
```

```
       10                  30                  50                  70                  90
        .         .         .         .         .         .         .         .         .
Pst CTGCAGGTTCCCTCCCGTTCCATTGAAAGGACTACACAATCACTGACGTTGTCATCTATCCGCCCCACCCGGTCGGCAAGTTTGGCGGC
                                       MetThrAspValValIleValSerAlaAlaArgThrAlaValGlyLysPheGlyGly 110                 130                 150                 170                 190
             .         .         .         .         .         .         .         .         .
TCGCTGGCCAAGATCCCGGAACTGGGCCTGCTCATCAAGCCCCTGAGCCGGGTCAAGCCGGAGCAGGTGAGCGAAGTC
SerLeuAlaLysIleProGluLeuGlyLeuLeuIleLysProLeuSerArgValLysProGluGlnValSerGluVal 210                 230                 250                 270
             .         .         .         .         .         .         .         .
ATCATGGGCCAGCTGCTGACCGCCGGGTTCGGGGTCCTGACCGCCGGCCAGAACCCGGCGATCAAGGCCCTGCCGGCGATGGTGCCCGGCCATGACC
IleMetGlyGlnValLeuThrAlaGlySerGlyValLeuThrAlaGlyGlnAsnProAlaIleLysAlaLeuProAlaMetValProAlaMetThr 290              310                 330                 350                 370
   .         .         .         .         .         .         .         .         .
ATCAACAACAAGCGCCGCCGCCCCACCTGCTCCGCCCTGAACCCCGTGATCCTGGCCGCCAACGGCGATCATGGCGGCCAACCCCGAGATCCTGGTGCCCGGGCCAG
IleAsnLysValCysGlyGlySerGlyLeuGlyLeuLysAlaValMetAlaAlaAsnAlaIleMetAlaGlyAspAlaGluIleLeuValValAlaGlyGlyGln 390                 410                 430                 450                 470
   .         .         .         .         .         .         .         .         .
GAAAACATGAGCGCCGCCCCCACCTGCTCCGCCCCTCGCCCGATGGTTCCGGCCATGGGCGATGCCAAGCTGGTTGACACCATGATCCTCGACGCC
GluAsnMetSerAlaAlaProHisValProGlySerArgAspGlyPheArgMetGlyAspAlaLysLeuValAspThrMetIleValAspGly 490                 510                 530                 550                 570
             .         .         .         .         .         .         .         .         .
CTGTGGGACGTGTACAACCAGTACAACCATCACCCCGAGAACGTGCCAAGGAATACGGCATCACGCGAGGCGAGGATGAGTTCGCC
LeuTrpAspValTyrAsnGlnTyrHisMetGlyIleIleThrAlaGluAsnValAlaLysGluTyrGlyIleThrArgGluAlaGluAspPheAla
```

```
                    590                         610                         630                         650                         670
                      .                           .                           .                           .                           .
GTCGGCTCCGCAGAACAAGGCCCGAAGCCGCCCCAGAAGCCGCCGCCAAGTTTGACGAAGAGATCTCTCCGGTGTCGATCCCCAGCGCAAGGGCGACCCG
 ValGlySerGlnAsnLysAlaGluAlaAlaGlnLysAlaGlyLysPheAspGluGluIleValProValLeuIleProArgLysGlyAspPro 690                         710                         730                         750
                      .                           .                           .                           .
GTGGCCTTCAAGACCGACGAGTTCGTGCGCCAGGGCGCCCTGACCGACGCCATGTCCGGCCTCAAGCCGCCTTCAAGCCGCACGTGACC
 ValAlaPheLysThrAspGluPheValArgGlnGlyAlaLeuThrLeuAspSerMetSerGlyLeuLysProAlaPheAspLysAlaGlyThrValThr 770                       790                         810                         830                         850
   .                         .                           .                           .                           .
GCGGCCAACGCCCTCGGGGCTGAACGACGGGCCCCCCCCTGTCGATGTCGGCGGCCAAGCCAAGGAACTGGGCCTGACCCCTGCGCCACG
 AlaAlaAsnAlaSerGlyLeuAsnAspGlyAlaValMetSerAlaAlaAlaLysAlaLysGluLeuGlyLeuThrProLeuAlaThr 870                         890                         910                         930                         950
                      .                           .                           .                           .                           .  Ava
ATCAAGAGCTATGCCAACCTGGACCTGATGGCGAGATCCCAAGGTCGATCCCGGCCATGGCCCCCCTGCGGCCGCCCTGCGGCCGAGTGGACC
 IleLysSerTyrAlaAsnAlaGlyValAlaAspProLysValMetGlyMetGlyProValProAlaSerLysArgAlaLeuSerArgAlaGluTrpThr 970                       990                         1010                        1030                        1050
   .  Ava                    .                           .                           .                           .
CCGCAAGACCTGGACCTGATGGAGATCAACGAGGCCCTTTGCCGCCTGGCCCTGCCGCCTCCACCAGCAGATGGGCTGGGACACCCTCCAAGGTCAAT
 ProGlnAspLeuAspLeuMetGluIleAsnGluAlaPheAlaAlaLeuAlaValHisGlnGluMetGlyMetGlyTrpAspThrSerLysValAsn 1070                        1090                        1110                        1130                        1150
                      .                           .                           .                           .                           .
GTGAACGGCCCCCCCATCGGCCACCCGGCCGCCGTCGGCCCGCTGAGCCCTGCCACCAGATCAAGCCCGGTGACGCG
 ValAsnGlyAlaIleGlyAlaIleIleGlyHisProIleGlyAlaSerGlyCysArgIleLeuValThrLeuLeuHisGluMetLysArgArgAspAla
```

```
                                                    1190              1210                       1230
AAGAAGGGCCTGGCCTCGCTGTGCTCGCATGGGCGGGGCGCATGGGCTGCCAGTGCCAGTCGAGCCAAATAAGGAAGGGGTTTCCGGGGCCCCGGCGCG
LysLysGlyLeuAlaSerLeuCysIleGlyGlyMetGlyValAlaLeuAlaValGluArgLys *
         1260              1280              1300              1320                       1340
         Ava               Dde
GTTGGCGGGACCCCGGCCCACCGATAACGAAGCCAATCAAGGAGACGACATGACTCAGCGCATTGCGTATGTGACCGGCCATGGTGTATGGA
                                            MetThrGlnArgIleAlaTyrValThrGlyMetGlyValIleGly
                                    1380              1400                       1420
ACCCCATTTGCCAAGGGCCTGGCCAAGGATGGCTTTCGTGTGCCCGGTTGCTGCGGGCCCCAACTCGCCCCCGGGCGAAAAGTGGCTGGAGCAGCAG
ThrAlaIleCysGlnArgLeuAlaLysAspGlyPheArgValAlaAlaGlyCysGlyProAsnSerProArgArgGluGluGluTrpLeuGluGlnGln
 1440                      1460              1480              1500                       1520
AAGGCCCTCGGCCTTCGAATTCATTGCCCTCGGAAGCCAATGTCCGAACCAATTCGACAAGCCCAAGTCCGAGTCGGC
LysAlaLeuGlyLeuArgIleHisCysProArgLysProMetSerGluThrAsnSerThrLysThrAlaPheAspLysProLysSerGluValGly
           1540              1560              1580                       1600                   1620
GAGGTTGATCTGCTGATCAACAACGCGGGTATCACCCCGGACGTGCTGTTCCGCAAGATGACCCGGAGCTGGATGCGGGTGATCGACACCAAC
GluValAspLeuLeuIleAsnAsnAlaGlyIleThrArgAspValLeuPheArgLysMetThrArgAlaAspTrpAspAlaValIleAspThrAsn
        1640              1660              1680              1700                   1720
CTGACCTCGCTGTTCAACGTCACCAAGCAGGTGATCCACGCCATGCTGGGCCGCAACCGTGGGCGTTGGGAGCGCATCTCTCGTCGTCAACCCGGCAG
LeuThrSerLeuPheAsnValThrLysGlnValIleHisAlaMetAlaAsnArgGlyTyrTrpGlyArgIleValAlaAsnIleSerSerValAsnGlyGln
       1740              1760              1780              1800                       1820
AAGGGCCCAGTTCGGCAACCAGCCAACTACTCCACCCCAAGGCCCTGATGGCCTTCAAGGCGATCGGCTTCACCATGGCACTGGAGCAGAAGTCCTGA
LysGlyGlnPheGlyAsnGlnProThrThrSerThrAlaLysAlaLeuGlyLeuHisGlyPheThrMetAlaLeuAlaLeuGluAlaGlnLysThrAlaGlyVal
       1840              1860              1880                       1900
ACCGTCAACACGGTCTCTCCGGGCTATATGCCAAGGCGATCGTCAAGGCGATCGTCAAGCAGATCCTCGACAAGATCCTCGACGATCCCGGCTC
ThrValAsnThrValSerProGlyTyrIleAlaThrAspMetValLysAlaIleArgGlnAspValLeuAspLysIleAlaIleThrIleProVal
```

```
1920                1940                1960                1980                2000
  .                   .                   .                   .                   .
AAGCGGCCTGGCCTGCCCGGAAGAGATCGCCTCGATCGCCTCGCCCTGTTGTCTCGGAGGAGTCCGTTTCTCGACCGGCCGACTTCTCGCTCAAC
LysArgLeuGlyLeuProGluIleLeuGluSerIleAlaSerIleCysAlaTrpLeuSerSerGluSerGlyPheSerThrGlyAlaAspPheSerLeuAsn 2020                2040                2060                2080                2100
  .                   .                   .                   .                   .
GGCGGCCTGCATATGGGCTGACCTGCCCGCTGGTCAACCAGTGTCGGCAGCCGGCTGGGTGCAGCCAGCGCGGCCACA
GlyGlyLeuHisMetGly *

2120                2140                2160                2180                2200
  .                   .                   .                   .                   .
AGGGCGGGGCGGTTCGTTTCGCGGCCCGTCAAGGGCCGTCAAGGCCGGGAATCGTTTCTGCCGGGCCATTCCTCGCTTTTGCCCAAT 2220                2240                2260                2280                2300
  .                   .                   .                   .                   .
TCACCGGGTTTCCTTAAGCCCGGCGTCGCTTTTCTTAGTCCCTTGTTGTGGGCATAGAATCAGGGCGGCAGCCAGCACCATGTTCGTGCAGCGC

2320
  .
GGCCCTCGGCGGGGCCAGCTGCAG
      Pst

FIGURE 3d
```

```
         Sma
    1   CCCGGGCAAGTACCTTGCCGACACTATGCGCTGGGCGCACGCGGCTGGCGGCGCGGCTGTACGGCGGCGACGCCTG         90
   91   CACCGTGGCCGAGCGCCGGTCGCTTCTACTCCTTGCCCCTGGGCGCCATGGCCGTCACCGCCGTTGGCTCTCGGCGGACTGAGC        180
  181   CGCCCCGTCCTCACTCGTCCTTGCCGCCGGGCCGCTCGGCGGCGCTCAGCGTCCGCGGGGGCGCTGCCCGGGGCTGCCCATGATG        270
  271   TAGAGCACCACGGCCACCGGGCCCATGCCATACATCAGGAAGGCTGGCCAACCACCTTGTCGTCGGTGATGGCCATCATCAGCG        360
  361   CCACGTAGAGCCAGCCAATGGCCACGATGTACATCAAAATTCATCCTCTCGGGGCTGGCAGATGGCGAGCGCTGCA        450
  451   TACCGTCGGTAGGTCGGAAGCGTGCAGTGCCGAGCCGATTCCGAGCCCGTTGCAAGGCAACAATGGACTCAAATG        540
  541   TCTCGGAATGCCTGACGATTCCCAGGTTCTCCCGCAAGCATAGCCATGGCGTCTCCATGGAGAATGTCGGCTTGCGCGGATAAAAGG         630
  631   GGAGCCGCTATCGGAATCGACGCAAGCCACGGCCAGGTGCGGTCGAGGGCTTCCAGCCAGTTCCAGGGCCAGATGTGCCGGCAGAC        720
  721   CCTCCCGCTTGGGGAGGCGCAAGCGCAAGCGGGTCCATTCGGATAGCATCTCCCCATGCAAAGTCCGGCCAGGGCAATCCCGAGCCGGTT        810
  811   CGAATAGTGACGGCAGAGACAATCAAATCATGGCGACAATCAAATGCTGAAGCTTCCACGCAGAAGGCAAGTCCAACCATTCAA        900
                                      M  A  T  G  K  G  A  A  A  S  T  Q  E  G  K  S  Q  P  P  F  K
  901   GGTCACCGCCGGGCCCATTCGATCCAGCGACACATGGCTGGAATGCTCGAAGGCAACGGCCACGCGGCGGCGGTC         990
         V  T  P  G  F  F  D  D  P  A  T  W  L  E  W  S  R  Q  W  Q  G  T  E  G  N  G  H  A  A  A  S
  991   CGGCATTCCGGCCTGGATGCGCTGGCAGGCGGTCAAGATGCCGGCGCAGCTCGGTGATATCCAGCAGCGCTACATGAAGGACTTCTC        1080
         G  I  P  G  L  D  A  L  A  G  V  K  I  A  P  A  Q  L  G  D  I  Q  Q  R  Y  H  K  D  F  S
 1081   AGCGGCTGTGGCAGGCCATGGCAGGGCCAAGGCCGAGGCGAATGGCAAGGCCGAGGCCACCGGTCCGCTCCACGACCGGCTTCCGGGACGGGCCATGGCGACCAA        1170
         A  L  W  Q  A  H  A  E  G  K  A  E  A  T  G  P  L  H  D  R  R  F  A  G  D  A  W  R  T  N
 1171   CCTCCCCATATCGCTTGCCTGCGTGGCGGGTTCACCTGCTCAATGCGGCGCATCCGTGAGGCGATCCAAGAC        1260
         A  L  W  Q  A  H  A  E  G  K  A  E  A  T  G  P  L  H  D  R  R  F  A  G  D  A  W  R  T  N
         L  P  Y  R  F  A  A  A  F  Y  L  L  N  A  R  A  L  T  E  L  A  D  A  V  E  A  D  A  K  T
```

*FIGURE 4a*

```
1261  CGGCCAGCGGCATCCGCTTCGCGATCTCGCAATGGCTCGCCCCAATCCGGAGGCGCAGGCCT  1350
      R  Q  R  I  R  F  A  I  S  Q  W  V  D  A  K  S  P  A  N  P  L  A  T  N  P  E  A  Q  R  L

1351  GCTGATCGAGTCGGGCGGCGAATCGCTCCGTGCGGGCGTGCGCAACATGATGAAGACCTCGACGGCCAAGATCTCGCAAGACGACGA  1440
      L  I  E  S  G  G  E  S  L  R  A  G  V  R  N  M  H  E  D  L  T  R  G  K  I  S  Q  T  D  E

1441  GAGCCGGTTTGAGTCGGCCGCCAATGTCGGCGGTCGACGTGTCTTCGAGAACGAGTACTTCCAGCTGTTGCAGTACAAGCC  1530
      S  A  P  E  V  G  R  N  V  A  V  T  E  G  A  V  V  F  E  N  E  Y  F  Q  L  L  Q  Y  K  P

1531  GCTGACGACAAGGTCCACGGCCGCCCGCTCCTGCATGTCCCCGTCAACAAGTACTACATCCTGGACCTGCAGCCGGAGAGCTC  1620
      L  T  D  K  V  H  A  R  P  L  L  H  V  P  P  C  I  N  K  Y  Y  I  L  D  L  Q  P  E  S  S

1621  GCTGGTGCGCCATGTGGTGGAGCAGGGACATACGGTGTTCTGTGGCCAATCCGGACGCCAGCATGGCCAGCACCTGGGA  1710
      L  V  R  H  V  V  E  Q  G  H  T  V  F  L  V  S  W  R  N  P  D  A  S  M  A  G  S  T  W  D

1711  CGACTACATCGAGCACGCCGCCATCCGCGCCATCGAAGTCGCCCGCGACATCAGCGGCCAAGACAAGATCAACGTCTCGGCTTCTGCGT  1800
      D  Y  I  E  H  A  A  I  R  A  I  E  V  A  R  D  I  S  G  Q  D  K  I  N  V  L  G  P  C  V

1801  GGGGGCCACCATTGTCTCGACACGGGCACCATCGTCGTCACCGTCGTGGCGCCGAGCACCCGGCGCAGCGTCAGCGTGCTGACCGCTGCT  1890
      G  G  T  I  V  S  T  A  L  A  V  L  A  A  R  G  E  H  P  A  A  S  V  T  L  L  T  T  L  L

1891  GGACTTTGCCGACACGGGCATCCTGGACGTCTTTGTGAACTCGAGGGCCATGTGCAGTTGCGGGCAGGCCGCTGGGGCCGCTGGGGAGACGCGC  1980
      D  F  A  D  T  G  I  L  D  V  F  V  D  E  G  H  V  Q  L  R  E  A  T  L  G  G  A  G  A

1981  GCCGTGCGCCTGCGCGGCCTTGAGCTGGCCAATACCTTCGTCTTGCGGCCGAACGACCTGGTGTGGAACTACGTGGTGACAA  2070
      P  C  A  L  L  R  G  L  E  L  A  N  T  F  S  F  L  R  P  N  D  L  V  W  N  Y  V  V  D  N

2071  CTACCTGAAGGCAACACCCCGGTCCGTTCGACCTGCTGTTCTGAACGGCGACGCCACCAACCTGCCGGGCGTGTACTGCTGTA  2160
      Y  L  K  G  N  T  P  V  P  F  D  L  F  W  N  G  D  A  T  N  L  P  G  W  Y  C  W  Y

2161  CCTGCGGGCCACTACCTGCAGAACGAGCTCAAGGTACCGGGCAAGCTGACCGTGTGCGGTGCCGGTGGACCTGGCCAGCATCGACGTT  2250
      L  R  H  T  Y  L  Q  N  E  L  K  V  P  G  K  L  T  V  C  G  V  P  V  D  L  A  S  I  D  V
```

*FIGURE 4b*

```
2251  GCCGACCTATATCTACGGCCTGGGCAGCGAAGACCATATCGTGCCGTGACGGGGCCTATGCCTGACCGCGCTGCTGGCGAACAAGCTGCGG   2340
      P  T  Y  I  Y  G  S  R  E  D  H  I  V  P  W  T  A  A  Y  A  S  T  A  L  L  A  N  K  L  R

2341  CTTCGTGCTGGGCGCGTCGGGCCATATCGCCGGTGTGATCAACCCGCCAAGAACAAGCGCAGCCACTGGACTAACGATGCGCTGCC       2430
      F  V  L  G  A  S  G  H  I  A  G  V  I  N  P  P  A  K  N  K  R  S  H  W  T  N  D  A  L  P

2431  GGAGTGCCCGCAGCAATGGCTAGCGGGCCATATCGAGCGGCATCACGGCAGCTGGCCGGACTGGTGCCGGACATGGCTGGCGGCAGGCGG   2520
      E  S  P  Q  Q  W  L  A  G  A  I  E  R  H  H  G  S  W  P  D  W  T  A  W  L  A  G  Q  A  G

2521  CGCCAAACGCCCGCGCCGCCAATCTATGGCAATACGGCCTATCCGCGGGATACGTCAAAGCCAAGGCATG                       2610
      A  K  R  A  A  P  A  N  Y  G  N  A  R  Y  R  A  I  E  P  A  P  G  R  Y  V  K  A  K  A  *

2611  ACGCTTGCATGAGTGCCGGCGTGCCGTCATGCACGGCCGGGCCTGCAGGTTCCCTCCCGTTCCATGAAAGGACTACACAATGAC        2700
                                             Pst                                           M  T

2701  TGACGTTGTCTCATCGTATCCGCGGCCCGCACCGGCGGTCGGCAAGTTTGGGGGCTGGCTGGCCAAGATCC    2768
      D  V  V  I  V  S  A  A  R  T  A  V  G  K  F  G  G  S  L  A  K  I
```

FIGURE 4C

```
       EcoR1
   1   GAATTCCTGCGGTGCACTCCCCTCCGCCGAGTCCAGGGCCAGGGTAACCCCATCCTGCAGTTCGGCAAGATCAACGTCGGCCTCAGC         90
  91   CGCCTGAACCTGCCCGCGGCCAATACCCACTGAACTTGACGCACGGCCATGACAGACGGCCCTGTTCACCTGGGAATACCTCGAGCAG        180
 181   CTGTGCCTGCCCGCAGGAACAGCTGTGGGCCGAGTACTGCACAAGGCCGGCGAATCCGCGACCCTGCCGAGTCGGCTGGTC              270
 271   AAACTCATGCTCTAGCGCAAGGCCTGCAGGATTTAGAGCGCATTTTCTAAAATCATCGTTTGAATGACTTACAGACAGCCCAGTGACCG        360
               Fsp1
 361   GCTGTCTTGCGCATTACATGAAAGTCGGGTAACCATGAAAGTCCCTGCATCAAATGCAGTAGTCAGAACCTGCAGCA                 450
                                                                                  →pPOB10
 451   CCGCTGTTCCTTATCACTGCTCTACCCGACTGCAGTACCCGGGCTCAGAACTGTGCACCGCCACAGCAACCGGTACTGCTCAGGACAA       540
 541   CGGAGACGTGTAGATGAGTAACAACAAGAGCAGCGCAGGCCTCAGCGGCCTGAAACACCCTGGGCTGAACCCGGTCATCGGTAT           630
              M  S  N  K  N  N  D  E  L  Q  R  Q  A  S  E  N  T  L  G  L  N  P  V  I  G  I
 631   CGGCCGCAAAGACCTGTTGAGCTCGGCACGCACCGTCTTGCGCCAGCCGCCCCTGCACAGCGCCAAGCATGTGGCCCACTT              720
         R  R  K  D  L  L  S  S  A  R  T  V  L  R  Q  P  P  L  H  S  A  K  H  V  A  H  F
 721   TGGCCTGAGCTGCAAGAACTGCTGGGCAAGTCCAGCTTGCCCCGGCAAGTCCAGCTTGCCCCGGCGAAAGCGACGACGTCAATGACCATGGAGCAA  810
          G  L  E  L  K  N  V  L  G  K  S  S  L  A  P  E  S  D  D  R  R  F  N  D  P  A  W  S  N
 811   CAACCCACTTACCCCGCTACCTACGCCAAACCTATCTGGCCTGGGCAAGGACTGGATGGCAACAGCGACTGTGCCCCA                 900
          N  P  L  Y  R  R  Y  L  Q  T  Y  L  A  W  R  K  E  L  Q  D  W  I  G  N  S  D  L  S  P  Q
 901   GGACATCAGCCGGGGCCAGTTCGTCATCAACCTGATGACCGAAGCCATGCTCCAACCCGTCCAACCGGCAGCAGTCAAACG             990
          D  I  S  R  G  Q  F  V  I  N  L  M  T  E  A  H  A  P  T  N  T  L  S  N  P  A  A  V  K  R
 991   CTTCTTCGAAACCGGCGGCAAGAGCCTGCTCGATGGCCTGTCCAACCTGGCCAAGGACCTGGTCAACAACGGCATGCACCCCAGCCAGGT    1080
          F  F  E  T  G  G  K  S  L  L  D  G  L  S  N  L  A  K  D  L  V  N  N  G  G  M  H  P  S  Q  V
1081   GAACATGGACGCCTTGAGGTGGGCAAGAACCTGGGCACCAGTGAAGGCGCGGTGTGTACCGAAGGATGTCTGGAGCTGATCCAGTA        1170
          N  M  D  A  P  E  V  G  K  N  L  G  T  S  E  G  A  V  V  Y  R  N  D  V  L  E  L  I  Q  Y
```

```
2251  ACCTGGGGACGCCACGGTGTTCATTTCACCCCATGAGTCACGGCCATGC      2300
                                                H  P
2701  AGGCAAGCCCAAGGTGTTGTGGATGATGGCCAGCCCGGTTAGTCAGCCGGTGCAGCCGTCATCGCCATTCGCCGACGATCTATGG  2790
       G  K  P  K  V  L  W  M  M  A  S  P  R  R  Y  V  Q  P  S  H  V  I  R  I  A  P  T  I  Y  G
2791  CGGCGGCTTCCGGCGTGACCCCGAACTGGCCAGCACGCCTCCAAGTGCGTCCGGGCAAGATGGGCTACTACTGGCAGCTGTT    2880
       G  G  F  R  R  D  P  E  L  A  H  Q  H  A  S  K  V  R  S  G  G  K  H  G  Y  Y  W  Q  L  P
2881  CGCCGGGCTCGGCTGGACCAGCATCCACTGGCTGCACAAGATCCAGCAGCCCACTGGTGCTGGCCGGCGACGACCCGTGATCCC    2970
       A  G  L  G  W  T  S  I  H  W  L  H  K  I  Q  Q  P  T  L  V  L  A  G  D  D  D  P  L  I  P
2971  GCTGATCAACACGGCCCTGCTGGCTCGGATTCCAAATGCCCAGCTACACATTATGGAGGAGGTCATTTGTCCTGATCACCGGGC   3060
       L  I  N  H  R  L  L  A  W  R  I  P  N  A  Q  L  H  I  I  D  D  G  H  L  F  L  I  T  R  A
                                                                                        Cla1
3061  CGAGGCCGTCGCCCCGATCATCATGAAGTTCCTTCAGCAAGAACGCCAGCGCGCCGTGCATGAACCCTCGCCCCGGCTTCCCGGGGGGTAAAT  3150
       E  A  V  A  P  I  I  M  K  F  L  Q  Q  E  R  Q  R  A  V  H  E  P  R  P  A  S  G  G  *
3151  CGATGCGGCCTTCTTCGGGGGCGCCCGCTCCCACAGGATGCGCCGAACCTGTGGAGCGGGCATGCCCGCCAAGGTCTGACAGCG   3240
                                                                M  P  A  K  V  S  T  A
3241  AAATGGCTTAGACGAGGGAGTGTGCCATGAAAGACAAACGGGCCAAGGAACGCCAACGTCGCCACCAGCCTTCCCGCCACGTTTCCGCCACGCCAAGGGACGCCCACGCCAAGAAC  3330
       K  W  L  R  R  G  S  V  A  H  K  D  K  P  A  K  G  T  P  T  L  P  A  T  S  H  N  V  Q  N
```

*FIGURE 6c*

```
3331  GCCATCCTCGGCCTGCGCGGTGTCGACCTGATTTCCACGCTGCGCAATGTCAGCCGCCAAAGCCTGCGTCACCCGCTCCACCCGGCACAT   3420
      A  I  L  G  L  R  G  R  D  L  I  S  T  L  R  N  V  S  R  Q  S  L  R  H  P  L  H  T  A  H

3421  CACCTGTTGGCCCTGGGTGCCAGCTGGGCGGGGCTGGGACAACTGGGTGATACTGGTCACACACGCTTCAGCGACATCGCGCTTCAGGGAC   3510
      H  L  L  A  L  G  G  Q  L  G  R  V  I  L  G  D  T  P  L  Q  P  N  P  R  D  P  R  F  S  D

3511  CCGACATGAGCCAGAACCCGTTCTACCGGCGGGGCCTGCAAGCCTACCTGGCTGGCACAAGCAGACCCGGCTGTGGATCGAGGAAAGC   3600
      P  T  W  S  Q  N  P  F  Y  R  R  G  L  Q  A  Y  L  A  W  Q  K  Q  T  R  L  W  I  E  E  S

3601  CACCTGGACGACGATGACCGGGCCGTGCCCACTCCTGTTCAACCTGATCAACGATGCCCTGGCGCCAAGCAACTGCTCGTCAACCG   3690
      H  L  D  D  D  R  A  R  H  P  L  P  N  L  I  N  D  A  L  A  P  S  N  S  L  L  N  P

3691  CTGGGCGGTCAAGGAACTGTTCAACAGCGGTTGGCGACGAGCCGTGGCCCACCTGGCCCACAGCCGCTGATGACCTGCGCACAATGACCGC   3780
      L  A  V  K  E  L  P  N  S  G  Q  S  L  V  R  G  V  A  H  L  D  D  L  R  H  N  D  G

3781  CTGCCACCGCAGTCGCAGGAGCGCCCTTGAAGTGGCGGCAACCTGGCCAACCTGGCCCGGCGCTGTGTTGCAAGAGCTGCTG   3870
      L  P  R  Q  V  D  E  R  A  P  E  V  G  G  N  L  A  A  T  A  G  A  V  V  F  R  N  E  L  L

3871  GAACTGATCCAGTACAAGCCGATGAGCGAAAAGCAGCAGCGCCCACTCTGGTGCGCCGCCCACAGATCAACAAGTTCTACATCTTC   3960
      E  L  I  Q  Y  K  P  M  S  E  K  Q  H  A  R  P  L  L  V  V  P  P  Q  I  N  K  F  Y  I  F

3961  GACCTCAGCTCGACCAACAGCTTCGTCCAGTACATGCTCAAGAATGGCCTGCAGGTGTTCATGGTCAGCTGGCGCAACCCGACCGGCGC   4050
      D  L  S  S  T  N  S  F  V  Q  Y  M  L  K  N  G  L  Q  V  F  H  V  S  W  R  N  P  D  P  R

4051  CACCGGGAATGGGCGCCTGCGCAGCAGCTACGTGCAGGCCCTGGAAGAAGCGCTCAACGCCTGCCGGAGCATTAGCGGCAACGGGGACCCCAAC   4140
      H  R  E  W  G  L  S  S  Y  V  Q  A  L  E  E  A  L  N  A  C  R  S  I  S  G  N  R  D  P  N

4141  CTGATGGGCGCCTGCGGCGGGCTGACCATGGCCGCAGCCCTGCAAGCACCAGCTGCCGCGTCGCAGCGGCC   4230
      L  M  G  A  C  A  G  G  L  T  H  A  A  L  Q  G  H  L  Q  A  K  H  Q  L  R  R  V  R  S  A

4231  ACCTACCTGGTCAGCTTGCTGGACAGCAAGTTCGAAAGCCCCTCCGCCACGAGCAGACCATCGAGGCCGCCAAGCGCCGC   4320
      T  Y  L  V  S  L  L  D  S  K  P  E  S  P  A  S  L  F  A  D  E  Q  T  I  E  A  A  K  R  R

4321  TCCTACCAGCGGGGCGTCCTCGATGGCGCCGAAGTGGCGCGCATCTTCGCCCAACGACCTGATTGGAACTACTGGGTC   4410
      S  Y  Q  R  G  V  L  D  G  A  E  V  A  R  I  F  A  W  H  R  P  N  D  L  I  W  N  Y  W  V
```

*FIGURE 6d*

```
4411  AACAACTACTGCTGGGAAGACACCAGCCTTGCAGATCCTGTACTGGAACGCGGACAGCACGCGCCTGCCCGCGGCTCATGGC   4500
      N  N  Y  L  L  G  K  T  P  P  A  F  D  I  L  Y  W  N  A  D  S  T  R  L  P  A  A  L  H  G

4501  GACTTGCTGGACTTCTTCAAGCTCAACCCGCTGACCCACCCGGCTGGAGCGGCTATGCGGAGCTGGAGGTCTGCGAGAAGCTGGAG   4590
      D  L  L  D  F  F  K  L  N  P  L  T  H  P  A  G  L  E  V  C  G  T  P  I  D  L  Q  K  V  E

4591  CTGGACAGTTTCACCGTGGCCGGCAGCAACGACCGAATCACCCCGTGGGATGCCGTGTACCGCTCGGCCTTGCTCGGTGGGACCGG   4680
      L  D  S  F  T  V  A  G  S  N  D  R  I  T  P  W  D  A  V  Y  R  S  A  L  L  L  G  G  D  R

4681  CGCTTGCTGTGCCAACAGCGGGCACATCCAGAGCATCATCAACCCCGGGCAAGGCCTACTACCTGGCCAACCCCAAGCTG   4770
      R  F  V  L  A  N  S  G  H  I  Q  S  I  I  N  P  P  G  N  P  K  A  Y  Y  L  A  N  P  K  L

4771  TCCAGCGACCCGCCGCGTGCCTGGCTCCACGATGCCAAGCGAGCACTGTGGCTCGAGTGGATCACCGCGGCTCC   4860
      S  S  D  P  R  A  W  L  H  D  A  K  R  S  E  G  S  W  H  P  L  W  E  W  I  T  A  R  S

4861  GCCCCGCTCAAGGCTCCGCGCAGCGAACTGGGCAATGCCACTTACCCACCCCGCCACTGTGCCTGACCGATGA   4950
      G  P  L  K  A  P  R  S  E  L  G  N  A  T  Y  P  P  L  G  P  A  P  G  T  Y  V  L  T  R  *

4951  GCATCCCGACTCGATGAAGACTCGGCCACCGTATCCTGCAGCTGTTCAACCAGCAGGGCGAACGGAAGTATCCACCCT   5040

5041  CGAAATTGCCAACGAACTGGGCATCAGCCCCTGCCAACTTCCAAGGCGAAGGACCGTTGGTGCTGGGGTTGTTCGAGCCG   5130

5131  CTTTGAAGAAGGCCTGATCCCCTGCTGAGACCGGCGAGCGCAGATTACTGGGTGTTCCTGCACCTGATCGT   5220

5221  CGAACGGCATGGCGCAGTACCGCTTCCTCCAGGACCTGCTGGGGCGGCCCTGCCAAACTGGGCCCGGGGCATGCGCAACCT   5310

5311  GATCAAGCGGCTCAAGCGCACACTGGGCGGCCGTTGCTGTAGAGACGGAGACCCAGGCGCTGGGGCA   5400

5401  ACTGGTGAGCAGATCACCCTGACACTGATGTTCTGCGATTATCAGCGGGTACTGGGCGCCAGGGGATGTGGGATTGTGGTGTA   5490

5491  CCAGGTGATGATGCTGTGCGGCCATGCTGCCAGGCCCGGGCCGGGGGCGGCGGAGCAATTGGCGGTGCGGTATCTGGAGGGTAAGC   5580
                                                                                Xho1
5581  CTGTTGATTGGCTGTGTGGGCTTCGGGGCATGCCCGCTCCCACAGGTGAAATCAGTGCTGAGTGCACACAGGACCGTGGGAGCCG   5670

5671  GCAAGCCGGCAAGATCGCAGGGGTATCAGATCAGGTACCGGTGTGTGTGCCGAAGGCCGGGTTGCTGCCGGAGCCGCAGTGG   5760
```

FIGURE 6e

```
5761  GCGCCGAAGCTGCGCTAGCGGCGGGGAGCGGCGCTGGCCGCTGGAGCTGCCCGGCTTGGCGGCTCCCGGTTGCCGGTGCTTCTTCACTG  5850
5851  CAGGCTTCTTCGCCACAGCCCGGTTTGCGGCTGCGCCGGTTCGCCCAGGCTTGGCGCCGCCAGTCTTGGCCAGCAGGTTTAGCCGCTGGGG  5940
5941  CCTTGGCTGCCGGCTTGGCTGGCGCTGGCGGGGTTTTTGCGCGGGCGGTTTGCGGCAGGCTTGGCGCTCTTGGCGGCCGGCCTTGCTCGGCAG  6030
6031  CCGGTTTGGCTGCAGTGGCGGACGAAATGGGGTAACGGGTGAGTTCTGGATCGCTGTGGTCAGGCTGTCCACCTGCTGGT  6120
6121  GCAGGGCCCTTGATCTGGTTGCGGCTGGGCCACGGCCAAGCGGGCAGATGGCACTGTTCAGGCGCTGTGTCGAAGGCCCTCTGCGAGTTGCTCC  6210
6211  ACTTGCCTAGCGCACGGTCCTTCAGCCCGGCAAGTGTCGACGACTTGGCAGTTTCAGCAAACATCTTCGCGGTCTTCTTC  6300
6301  GCCTGTTTCTCGGCCTTCTCGCCCATCCTTACCAGCGCAAGCTTCGGGCCGTCGATCTTCGAATAGATACCAAGCCCC  6390
6391  GCCAGCCAGATCTTGCGGAGTACTTCTCGATCCCGACCAGAGCGCCTTCTTTCTGGAATTC  6459
                                                       EcoR1
```

*FIGURE 6f*

POLYHYDROXYBUTYRATE POLYMERASE

This is a continuation of U.S. Ser. No. 09/935,244, filed Aug. 21, 2001, now U.S. Pat. No. 6,528,706 entitled "Polyhydroxybutyrate Polymerase", by Oliver P. Peoples and Anthony J. Sinskey, which is a continuation of U.S. Ser. No. 08/922,007, filed Sep. 2, 1997, now abandoned, which is a continuation of U.S. Ser. No. 08/438,611 filed May 10, 1995, now U.S. Pat. No. 5,663,063; which is a divisional of U.S. Ser. No. 08/418,868 filed Apr. 7, 1995, now U.S. Pat. No. 5,534,432; which is a continuation of U.S. Ser. No. 08/234,721 filed Apr. 28, 1994, now abandoned; which is a continuation of U.S. Ser. No. 08/073,603 filed Jun. 7, 1993, now abandoned; which is a continuation of U.S. Ser. No. 07/944,881 filed Sep. 14, 1992, now abandoned; which is a divisional of U. S. Ser. No. 07/700,109 filed May 8, 1991, now U.S. Pat. No. 5,245,023; which is a continuation of U.S. Ser. No. 07/378,155 filed Jul. 10, 1989, now abandoned; which is a continuation-in-part of U.S. Ser. No. 07/067,695, filed Jun. 29, 1987, now abandoned.

The United States government has rights in this invention by virtue of grants from the National Institute of Health, Office of Naval Research, and National Science Foundation.

Synthesis by bacteria has long been the only means for production of many of the more complex biopolymers. Only recently have pathways for the synthesis of these polymers been determined. Much effort has gone into the isolation of the various enzymes and cofactors involved in these pathways. Regulation of their expression has largely been empirical, i.e., the concentration of nutrients or other factors such as oxygen level have been altered and the effect on polymer production and composition measured.

In order to have control over the production of these complex biopolymers, and to modify them in a specific fashion, it is necessary to design a system for determining the chemical steps required for their synthesis; to isolate and characterize the proteins responsible for these chemical steps; to isolate, sequence, and clone the genes encoding these proteins; and to identify, characterize, and utilize the mechanisms for regulation of the rate and level of the expression of these genes.

Polyhydroxybutyrate, a commercially useful complex biopolymer, is an intracellular reserve material produced by a large number of bacteria. Poly-beta-hydroxybutyrate (PHB), the polymeric ester of D(-)-3-hydroxybutyrate, was first discovered in *Bacillus megaterium* in 1925. Both the chemical and physical properties of this unique polyester have made it an attractive biomaterial for extensive study. PHB has a variety of potential applications, including utility as a biodegradable/thermoplastic material, as a source of chiral centers for the organic synthesis of certain antibiotics, and as a matrix for drug delivery and bone replacement. In vivo, the polymer is degraded internally to hydroxybutyrate, a normal constituent of human blood.

The enzymatic synthesis of the hydrophobic crystalline PHB granules from the $C_2$ biosynthon acetyl-CoA has been studied in a number of bacteria. Three enzymes: beta ketothiolase, acetoacetyl-CoA reductase and PHB polymerase, are involved in the conversion of acetyl-CoA to PHB.

Thiolases are ubiquitous enzymes which catalyze the synthesis and cleavage of carbon-carbon bonds and thus occupy a central role in cellular metabolism. Different thiolase enzymes are involved in terpenoid, steroid, macrolide and other biosynthetic pathways as well as the degradation of fatty acids. In *Z. ramigera*, the condensation of two acetyl-CoA groups to form acetoacetyl-CoA is catalyzed by beta-ketothiolase. The acetoacetyl-CoA is then reduced by an NADP-specific reductase to form D(-)-beta-hydroxybutyryl-CoA, the substrate for PHB polymerase.

Beta-Ketothiolase (acetyl-CoA-CoA-C-acetyl-transferase, E.C. 2.3.1.9) has been studied in *A. beijerinckii* (Senior and Dawes, *Biochem. J.*, 134, 225–238 (1973)), *A. eutrophus* (Ceding and Schlegel, *Biochem, J.*, 134, 239–248 (1973)), *Clostridium pasteurianum* (Bernt and Schlegel, *Arch. Microbiol.*, 103, 21–30 (1975)), and *Z. ramigera* (Nishimura et al., *Arch. Microbiol.*, 116, 21–27 (1978)). The cloning and expression of the *Z. ramigera* acetoacetyl-CoA reductase genes was described in U.S. Ser. No. 067,695. This gene was then used as a hybridization probe to isolate the reductase gene from other bacterial species, including *Alcaligenes eutrophus* and *Nocardia*.

The reductase involved in PHB biosynthesis in *Z. ramigera* is stereospecific for the D(-)-isomer of hydroxybutyryl-CoA and uses NADP(H) exclusively as a cofactor. The best characterized Acetoacetyl-CoA reductase is that from *Zoogloea*, described by Saito et al., *Arch. Microbiol.*, 114, 211–217 (1977) and Tomita et al., *Biochemistry of Metabolic Processes*, 353, D. Lennon et al., editors (Elsevier, Holland, 1983). This NADP-specific 92,000 molecular weight enzyme has been purified by Fukui, et al., *Biochim. Biophys. Acta* 917, 365–371 (1987) to homogeneity, although only in small quantities. As described in U.S. Ser. No. 067, 695, the beta-ketothiolase enzyme from *Z. ramigera* has now been cloned, expressed and the product thereof purified to homogeneity. The cloned gene was used to identify and isolate the corresponding beta-ketothiolase gene in other bacterial species, including *Alcaligenes eutrophus* and *Nocardia*.

The PHB polymerise in *Z. ramigera* is stereospecific for D-beta-hydroxybutyryl CoA. Synthetases from other bacteria such as *A. eutrophus* can utilize other substrates, for example, D-beta-hydroxyvaleryl CoA, since addition of propionate into *A. eutrophus* cultures leads to incorporation of $C_5$ and $C_6$ units into a PHB/HV copolymer. Griebel and Merrick, *J. Bacteriol.*, 108, 782–789 (1971) separated the PHB polymerase from native PHB granules of *B. megaterium*, losing all of the enzyme activity in the process. They were able to reconstitute activity only by adding PHB granules to one of two fractions of the protein. More recently, Fukui et al., *Arch. Microbiol.*, 110, 149–156 (1976) and Tomita et al. (1983), investigated this enzyme in *Z. ramigera* and partially purified the non-granule bound PHB polymerase. A method for cloning, expressing and using the product thereof in the synthesis of novel polymers was described in U.S. Ser. No. 067,695.

A whole range of polyhydroxalkanoate (PHA) storage polymers has been found to be produced by bacteria, including *A. eutrophus* and *P. oleovarans*. The PHA polymers are heteropolymers of the D-isomer of β-hydroxyalkanoates with the variation occurring in the length of the side chains ($CH_3$—$CH_8H_{17}$). For example, when grown in the, presence of 5-chloropentanoic acid, *A. eutrophus* incorporates 3-hydroxybutyrate, 3-hydroxyvalerate and 5-hydroxyvalerate into the polymer.

Given the extremely high yields of this polymer obtainable through classic fermentation techniques, and the fact that PHB and PHA of molecular weight greater than 10,000 is useful for multiple applications, it is desirable to develop new PHB-like biopolymers to improve or create new applications.

The production of poly-beta-hydroxyalkanoates, other than PHB, by monocultures of *A. eutrophus* and *Pseudomonas oleovorans* was reported by deSmet, et al., in *J.*

*Bacteriol.*, 154, 870–878 (1983). In both bacteria, the polymers were produced by controlled fermentation, *A. eutrophus*, when grown on glucose and propionate, produces a heteropolymer of PHB—PHV, the PHV content reaching approximately 30%. *P. oleovorans* produces a homopolymer of poly-beta-hydroxyoctanoate when grown on octane. *Nocardia* has been reported to form copolymers of PHB-PH-2-butenoate when grown on n-butane. Determination of the final composition of 3-hydroxybutyrate polymers by controlled fermentation using selected substrates is also disclosed in U.S. Pat. No. 4,477,654 to Holmes et al.

With the availability of a variety of enzymes varying as to their substrate specificity and techniques for expressing the genes encoding the enzymes in other hosts, especially plants, it is possible to provide an economic, biodegradable alternative to the presently available plastics derived from petroleum, especially polypropylene.

It is therefore an object of the present invention to provide further enzymes for use in a method for synthesis of complex biopolymers, particularly PHB, PHA and similar polymers.

It is a further object or this invention to isolate, sequence, and clone additional genes encoding these proteins for polymer synthesis, as well as means for regulation of the rate and level of the expression of these genes.

It is another object of the present invention to provide purified proteins expressed from the genes encoding the proteins for synthesis of polyhydroxybutyrate and polyhydroxyalkanoate.

It is a further object of the present invention to provide methods for using these proteins and regulatory sequences to create novel biopolymers having polyester backbones.

It is a still further object of the present invention to provide an economic source of biodegradable polyhydroxyalkanoates and novel related polymers, using both bacterial and plant cells for production.

SUMMARY OF THE INVENTION

A method for controlling and modifying biopolymer synthesis by manipulation of the genetics and enzymology of synthesis of polyhydroxybutyrate (PHB) and polyhydroxyalkanoate (PHA) polyesters at the molecular level in procaryotic and eukaryotic cells, especially plants.

Examples demonstrate the isolation, characterization, and expression of the genes involved in the production of PHB and PHA polymers. Genes encoding the enzymes in the PHB and PHA synthetic pathway (beta-ketothiolase, acetoacetyl-CoA reeducates and PHB polymerise or PHA polymerase) from *Zoogloea ramigera* strain I-16-M, *Alcaligenes eutrophus, Nocardia salmonicolur*, and *Pseudomonas olevarans* were identified or isolated and expressed in a non-PHB producing organism, *E. coli*.

In a preferred embodiment using bacterial cells, the polymer is made in *A. eutrophus* due its capacity for accumulating PHB up to 70 to 80% dry cell weight under conditions of nitrogen or phosphate limitation. In another embodiment, the genes are introduced into plant cells for expression and synthesis of PHB, PHA, and novel polymers. Specific modifications to the polymers include variation in the chain length of the polymers and incorporation of different monomers into the polymers to produce co-polymers with different physical properties,

BRIEF DESCRIPTION OF THE DRAWINGS

FIG. 2 is the complete nucleotide sequence of 2.3 kb of *Z ramigera* DNA located downstream from the thiolase gene in clone pUCDBKl, encoding the acetoacetyl CoA reductase. The sequence of 2094 bp extending from the first SalI site to the second Smal site is shown. Also shown is the translation product of the acetoacetyl-CoA reductase structural gene extending from the ATG at nucleotide 37 to nucleotide 758 before the TGA stop codon at nucleotide 759. Boxed amino acid residues 2 to 6 are identical to those obtained by Edman degradation of the purified protein. A potential ribosome binding site is underlined and a potential transcription terminator is indicated by arrows. Restriction sites for SalI and Smal are shown.

FIG. 3 shows the nucleotide sequence of a corresponding 2 kb fragment *A. eutrophus* DNA cloned in plasmid pAeT3. The translation products of the *A. eutrophus* thiolase and acetoacetylase-CoA reductase genes extending from nucleotides 40 to 1219 and 1296 to 2033, respectively, are shown. Restriction endonuclease cleavage sites used in the construction of the overproduction vectors pAT and pAR are shown. Pst 1=Pst 1; Ava=2 and Dde=Dde 1.

FIG. 4 is the nucleotide sequence of the PHB polymerase (phbC) locus of *Alcaligenes eutrophus H*16. The translation product of the open reading frame from position 842 to position 2608, the predicted amino acid sequence of PHB polymerase is shown. Also shown is the translation product of the first 72 nucleotides of the phbA gene. A sequence capable of forming a hairpin structure (position 2660) is indicated by the arrows.

FIG. 6 is the nucleotide sequence analysis of the complete 6 kb fragment containing the *P. oleovarans* phbC gene.

DETAILED DESCRIPTION OF THE INVENTION

Figure 1A:
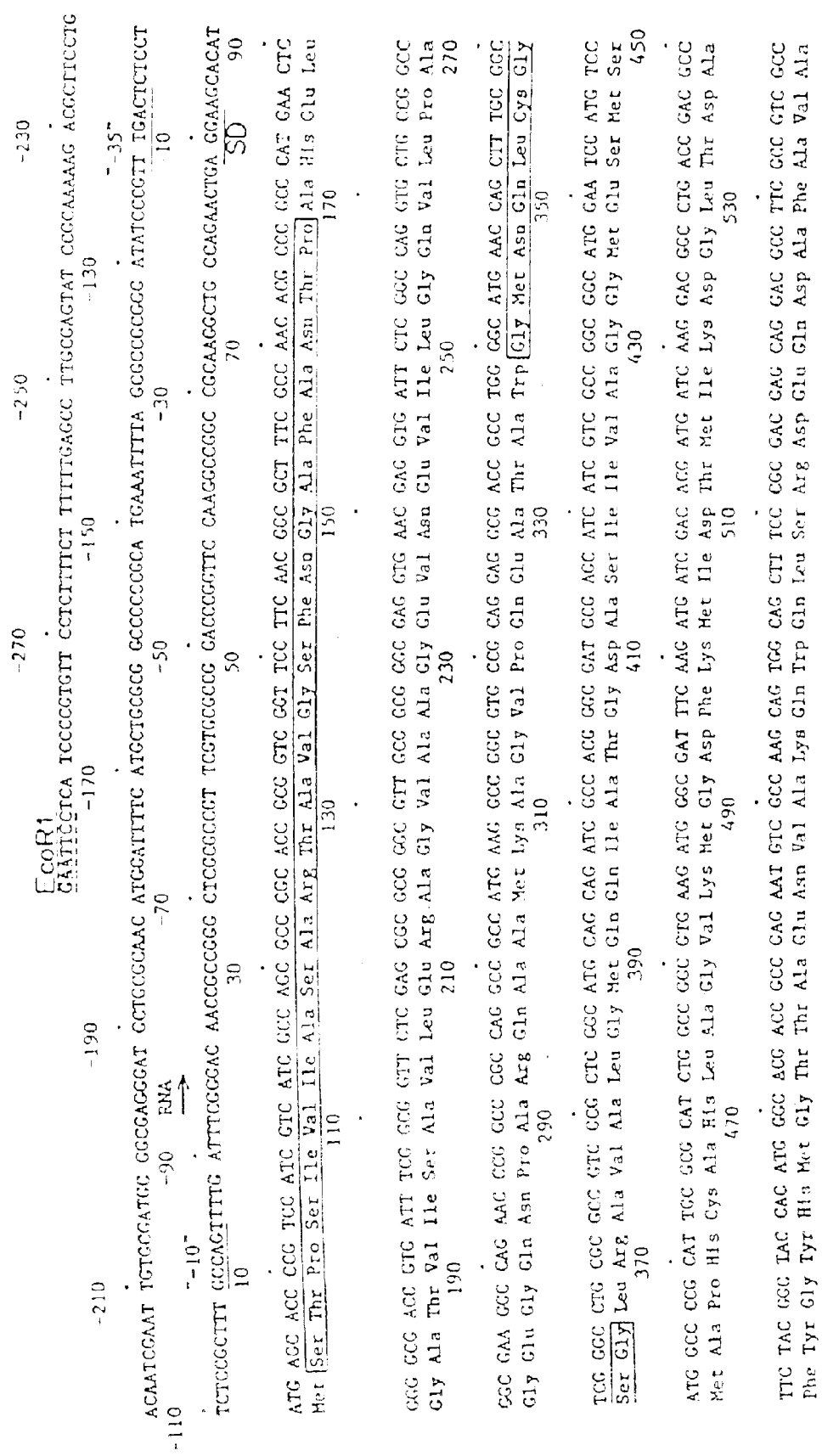
FIG. 1 is the thiolase gene sequence from *Zoogloea ramigera*. The sequences located at positions homologous to the *E. coli* "−10" and "−35" consensus regions (−100 to −95 and −122 and −116) upstream from the transcription start site (bold arrow) are underlined. A probable ribosome binding site is underlined (−11 to −8).

The following methods were used to isolate genes encoding beta-keto thiolase, acetoacetyl-CoA reductase, PHB polymerise, and PHA polymerise, and their expression products, to identify and characterize sequences regulating their expression, and to determine the effect of culture conditions and substrate availability on polymer production. Techniques for constructing systems for the production of PHB and PHA-like biopolymers are also disclosed. By combining these enzymes in either bacterial or plant cells with the appropriate substrates under controlled culture conditions of available oxygen and temperature, a variety of polymers can be constructed. The enzymes or nucleotide sequences controlling their expression can also be modified to alter the quantity of expression or substrate specificity to further vary the resulting polymers. An added advantage is that substrates which normally cannot be used with whole cells can be manufactured using the isolated enzymes.

The methods, genes, and products of their expression and polymer synthesis are described in detail in the following non-limiting examples.

Media and Culture Conditions

*Zoogloea ramigera* strain I-16M (ATCC 19623) was used initially to study the genetics of the PHB bio-synthetic pathway. *Z. ramigera* DNA was purified from 200 ml mid-log phase cultures as follows: cells were harvested by centrifugation, washed in 20 mM Tris-HCl, pH 8.2, and resuspended in 10 ml of Tris-HCl. The cells were then spheroplasted by the addition of 10 ml of 24% w/v polyethylene glycol 8000 and 2 ml of 25 mg/ml lysozyme, followed by incubation at 37° C. for 30 min. The spheroplasts were harvested by centrifugation, resuspended in 5 ml of TE buffer (10 mM Tris-HCl pH 8.0, 1 mM EDTA), 300 microliters of 10% w/v SDS added, and the cells lysed by incubating at 55° C. for 10 min. An additional 10 ml of TE was added and the lysate incubated with RNAse (50 microgram/ml) and proteinase K (30 microgram/ml) for 1 h at 37° C. The DNA was then purified by CsCl gradient centrifugation.

*E. coli* strains were grown in LB (Luria Bertani) medium, (NaCl, 10 g/l; Tryptone, 10 g/l; yeast extract, 10 g/l) or 2XTY medium (NaCl, 5 g/l; Tryptone, 16 g/l; yeast extract, 10 g/l). For the production of PHB or PHA by *E. coli* containing recombinant plasmids, minimal media was used, with the modification that the $(NH_4)_2SO_4$ concentration was decreased to 0.04%.

*A. eutrophus* strains were grown in Trypticase soy broth (TSB, BBL Microbiology systems, Cockeysville, Md.) or a defined minimal medium composed of 0.39 g/l $MgSO_4$; 0.45 g/l $K_2SO_4$; 12 ml 1.1 m $H_3PO_4$; 15 mg/l $FeSO_4.7H_2O$; 24 ml trace elements (20 mg/l $CuSO_4.5H_2O$; 100 mg/l $ZnSO_4.6H_2O$; 100 mg/l $MnSO_4.4H_2O$; 2.6 g/l $CaCl_2.2H_2O$). The pH was adjusted to 6.8 with NaOH and the medium sterilized by autoclaving. $NH_4Cl$ was added to a final concentration of 0.1% or 0.01% as nitrogen source and fructose was added to a final concentration of 0.5–1% (w/v).

Plasmid DNA preparations were carried out using the method of Birnboim and Doly in *Nucleic Acids Res.*, 7, 1513–1523 (1979) as described by Ish-Horowicz and Burke, *Nucleic Acids Res.*, 9, 2989–2998 (1981). Lambda DNA was prepared by standard procedures described in Maniatis et al., *Molecular Cloning: A Laboratory Manual.* (Cold Spring Harbor Laboratory, Cold Spring Harbor , N.Y. 1982). DNA sequence analysis was carried out using the M13mp18 and M13mp19 cloning vectors (Yanisch-Perron, et al., *Gene* 33,103–109 (1985)) and the dideoxy chain termination procedure of Sanger, et al., *Proc. Natl. Acad. Sci. USA* 74, 5463–5467 (1977). α-[$^{35}$S]-dATP and the Klenow fragment of DNA polymerase 1 were purchased from Amersham. Sequence data were compiled and analysed on a VAX system.

A recombinant library of random *Z. ramigera* chromosomal DNA fragments was constructed using the lambda gtll expression vector described by Young and Davis; *Science*, 222, 778–782 (1983). *Z. ramigera* DNA was first methylated using EcoRI methylase and then partially digested with DNAse 1 in the presence of $Mg^{2+}$, as taught by Anderson, *Nucleic Acids*, 9, 3015–3026 (1981). The ends of the partially digested DNA fragments were repaired using Klenow polymerase, EcoRI linkers added, and the DNA digested to completion with an excess of EcoRI. Fragments of 2–8 kb were size-selected on a 1.5% agarose gel, purified by electroelution, and ligated with ExoRI-digested phosphatased labda gtll DNA. Ligations were carried out for 18 h at 4° C. using 2 micrograms of lambda gtll DNA and 1 microgram of fragmented chromosomal DNA in a total volume of 10 microliters. The complete ligation reactions were packaged in vitro using lambda extracts prepared from *E. coli* strains BHB2688 and BHB2690, Hohn and Murray, *Proc. Natl. Acad. Sci., USA*, 74, 3259–3263 (1977), as described by Maniatis et al. (1982). Packaged phage were plated out and amplified on *E. coli*, Y1088.

Screening of the lambda gtll expression library was carried out using rabbit anti-thiolase antibodies and a modification of the procedure described by Young and Davis, *Science*, 222, 778–782 (1983).

Restriction endonucleases, T4 DNA ligase and DNA polymerase 1 were obtained from New England Biolabs and used under conditions provided by the manufacturer. Calf intestinal alkaline phosphatase was purchased from Boehringer Mannheim Corporation. All routine DNA manipulations, including plasmid purifications, *E. coli* transformations, etc. were performed using methods described by Maniatis, et al. (1982). Chromosomal DNA was purified from *A. eutrophus* strains, grown to late logarithmic phase in TSB. Transfer of restriction digested DNA samples from agarose gels to nitrocellulose filters, prehybridization and hybridization with $^{32}$P-labelled DNA probes was as described by Peoples, et al., *J. Biol. Chem.* 262, 97–102 (1987). Rapid plasmid isolation from *A. eutrophus* recombinant strains for restriction analysis were performed by the alkaline extraction procedure of Birnboim and Doly, *Nucleic Acids Res.*, 7, 1513–1523 (1979).

Conjugation in *A. eutrophus*

The conjugal transfer of the broad host range plasmid, pLAFR3, or recombinant derivatives of pLAFR3, into *A. eutrophus* was performed using the method described by Easson et al, *J. Bacteriol.* 169, 4518–4524 (1987). In this case, however, the recipient *A. eutrophus* cells were not sonicated and transconjugants were selected on *A. eutrophus* mineral agar plates containing 0.01% $NH_4Cl$ as nitrogen source, 1% (w/v) fructose as carbon source and 10 μg/ml tetracycline.

For Tn5 mutagenesis, a spontaneous streptomycin resistant strain of *A. eutrophus* 11599 (1599 S1) was used. Transfer of PRK602 (Tn5) was carried out as described above using *E. coli* MM294A (pRK602) as the only donor. *A. eutrophus* strains containing Tn5 were selected for by growth on streptomycin (500 μg/ml) and kanamycin (100 μg/ml).

Identification of the *Z. ramigera* Thiolase Gene

Thiolase antiserum was prepared in New Zealand White female rabbits, using purified thiolase protein by standard procedures. Antibody titer was estimated by the Ouchterlony double-diffusion assay, *Acta Pathol. Microbiol. Stand.* 26, 507–515 (1949). Purified antibody was prepared from the serum by chromatography on protein A agarose according to Bighee et al., *Mol. Immunol*, 20, 1353–1357 (1983). Approximately $4 \times 10^4$ recombinant phage adsorbed to *E. coli* Y1090 were plated out on 15 cm LB-agar plates and incubated at 42° C. for 3 h. The plates were then overlayed with nitrocellulose filters (Schleicher & Schull, BA85), which had previously been saturated in 10 mM IPTC, and incubated a further 4 h at 37° C. Filters were removed, washed for 10 min in TEST (50 mM Tris-HCl, pH 7.9 150 mM NaCl, 0.05% Tween-20), incubated in TEST plus 20% v/v fetal calf serum for 30 min, and rinsed in TBST. First antibody was bound by incubating the filters in 10 ml TBST plus purified anti-thiolase antibody (10 microliters) for 1 h at room temperature. The filters were subsequently washed in three changes of TBST for 5 min each time. Bound first antibody was detected using a biotin-avidin horseradish peroxidase detection system (Clontech Laboratories) and horseradish peroxidase color development reagent (Bio-Rad Laboratories, Richmond, Va.), Proteins were separated by sodium dodecyl sulphate-polyacrylamide gel electrophoresis according to the method of Laemmli, *Nature* 222, 680–685 (1970) and electrophoretically transferred to nitrocellulose filters (Schleicher & Schuill BA85), essentially as described by Burnette, *Anal. Biochem.* 112, 195–203 (1981). Following transfer overnight at 30 V, filters were rinsed in TBS (TBST without Tween-20) and incubated in TBS plus 5% bovine serum albumin. Proteins reacting with anti-thiolase serum were then detected by incubating the filters in 100 ml of TBS, 1% gelatin containing 2 ml of anti-thiolase serum for 1–2 h. Bound first antibody was subsequently detected using goat anti-rabbit IgG horseradish peroxidase conjugate and horseradish peroxidase color development reagent (Bio-Rad Laboratories, Richmond, Calif.).

DNA blots were prepared using DNA fragments separated on agarose gels by the sandwich blot method of Smith and Summers, *Anal. Biochem*, 109, 123–129 (1980) based on the technique developed by Southern, *J. Mol. Biol*, 98, 503–517 (1975). Filters were hybridized with DNA probes labeled to a high specific activity (0.1–1×10$^8$ cmp/μg of DNA) with [α-$^{32}$P]dATP, by nick translation, Rigby et al., *J Mol. Biol.*, 113, 237–251 (1977). Prehybridizations and hybridizations were carried out at 65° C. in sealed polythene bags. The prehybridization/hybridization solution contained 5×SSCP (1×SSCP contains 0.15 M NaCl, 0.15 M sodium citrate 10 mM Na$_2$HPO$_4$, 10 mM NaH$_2$PO$_4$), 5×Denhardt's solution, 0.1% (w/v) SDS, 10 mM EDTA, and 100 μg/ml sonicated denatured salmon DNA. Filters were prehybridized for 8–18 h and hybridized for 16–18 h using 10$^7$ Cpm of labeled DNA probe per filter.

Lysogens of lambda gtll recombinant clones were prepared in *E. coli* Y1089 as described by Young and Davis, *Science* 222, 778–782 (1983). For the preparation and analysis of lambda-coded proteins, lysogens were grown at 30° C. in LB (100 ml) until they reached an OD$_{500}$ of 0.5. The prophage was induced by a 20 min incubation at 45° C., IPTG added to 5 mM and the induced lysogens incubated at 37° C, for 1 h. Cells were harvested, resuspended in assay buffer (0.1 M Tris-HCl, pH, 7.5, 5 mM beta-mercaptoethanol, 5% (v/v) glycerol, lysed by sonication, cell debris pelleted by centrifugation, and the cell extracts stored at −20° C. The protein concentrations of bacterial lysates were assayed by the method of M. M. Bradford in *Anal. Biochem.* 72, 248–254 (1976), using bovine serum albumin as a standard. Thiolase-enzyme assays were performed as described by Nishimura, et al. *Arch. Microbiol*, 116, 21–27 (1978).

DNA fragments were cloned into the M13 vectors mp10 and mp11 and sequenced by the dideoxy chain-termination method of Sanger et al., *Nucleic Acids Res.* 10, 141–158 (1980), *Proc. Natl. Acad. Sci, USA* 74, 5463–5467 (1977). The M13 sequencing primer and other reagents were purchased from Amersham Corp. G/C rich regions were resequenced using dITP in place of dGTP as described by Mills and Kramer, *Proc. Natl. Acad. Sci. USA* 76, 2232–2235 (1979). Computer-assisted sequence analysis was accomplished using the Staden programs. *Acid Res* 10, 141–158 (1984).

Approximately 2×10$^5$ recombinants were obtained from 1 μg of purified target DNA, and amplified in *E. coli* Y1088. A total of 10$^5$ amplified phage were screened using purified rabbit anti-thiolase antibodies. The initial screening identified 10 potentially positive clones (LDBK1–LDBK10). Analysis by restriction digestions demonstrated that clones LDBK2–10 are identical. Clones LDBK1 and LDBK2 were selected for further study. LDBK1 has an insert composed of 2 EcoRI fragments of 3.6 kb and 0.75 kb. LDBK2 has an insert composed of 3 EcoRI fragments of 1.65 kb and 1.08 kb.

The proteins coded for by the: LDBK1 and LDBK2 insert sequences were analyzed both for thiolase-enzyme activity and for cross-reaction to rabbit anti-thiolase serum. Lysogenic strains of *E. coli* Y1089 containing LDBK1 and LDBK2 phage DNA were prepared. Several lysogens were obtained for each clone and two of these, Y1089/LDBL1 and Y1089/LDBK2, were used for subsequent studies. A lysogen of the lambda gtll vector, BNN97/lambda gtll, was used as a control. The results of the thiolase-enzyme assays clearly indicate that the proteins from Y1089/LDBK1 contain a substantial amount of thiolase activity. Furthermore, the thiolase activity is inducible, greater than 5-fold, by the addition of IPTG. This shows that expression of the thiolase-coding sequences is under the transcriptional control of the lac promoter contained in the lambda gtll vector. Neither the Y1089/LDBK2 nor the BNN97/lambda gtll protein lysates demonstrate any significant thiolase-enzyme activity even when induced with IPTG.

The size of the proteins responsible for the initial positive reaction to rabbit anti-thiolase antibodies was investigated by Western blot experiments. Protein lysates were separated by SDS-polyacrylamide gel electrophoresis, transferred to nitrocellulose filters, and screened with rabbit anti-thiolase serum. The results show an immunoreactive 40,000 dalton protein in both the IPTG-induced and non-IPTG-induced lysate of Y1089/LDBK1.

The LDBK1 insert was restriction mapped. The large 3.6 kb EcoRI fragment, containing the complete thiolase gene region, was subcloned into the plasmid vector pUC8 for ease of manipulation. Restriction analysis of one of the subclones obtained, pUCDBKl, confirmed the restriction map of this fragment in LDBK1. pUCDBKl DNA-was labeled to a high specific activity with $^{32}$P and hybridized to nitrocellulose filters containing *Z. ramigera* chromosomal DNA digested with the same enzymes used to restriction map pUCDBKl. Southern hybridization experiments confirm that the 5.4 kb genomic fragment hybridizes to both a 1.45 kb SalI/EcoRI and 1.05 kb SalI fragment from pUCDBKl. Based on the result of Southern hybridization experiment, the cloned pUCDBKl insert is represented in the *Z. ramigera* genome only once.

Figure 1B:
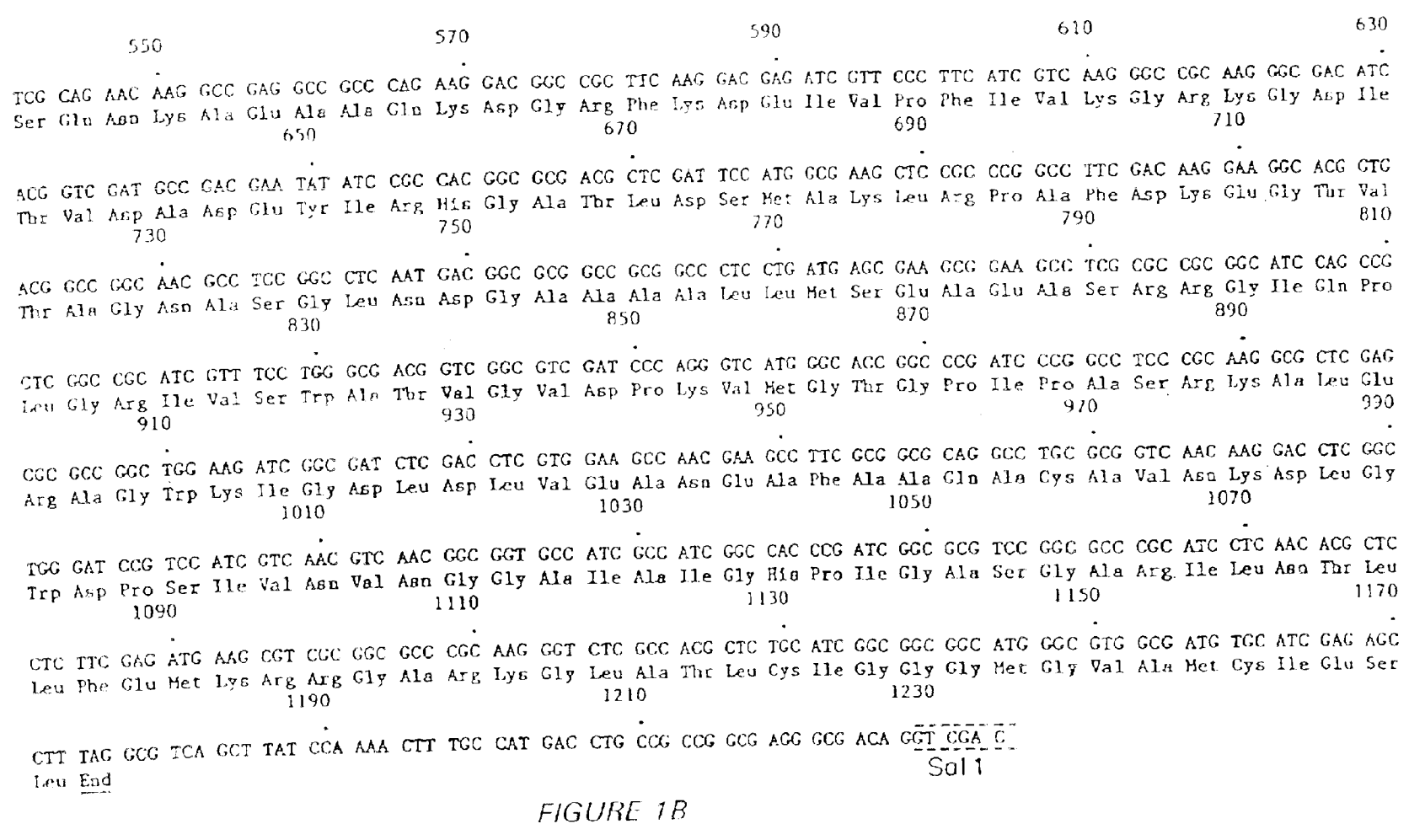

DNA sequence analysis of the pUCDBKl insert was carried out using the M13/Sanger dideoxy chain termination method. To locate the gene-coding region, individual DNA sequences were scanned in all six reading frames for homology to the NH$_2$-terminal amino acid sequence. By using this approach, the gene-coding region within the 1.45 kb EcoRI/SalI fragment was identified. The complete nucleotide sequence of the plus strand of the gene is shown in FIG. 1. 290 bp downstream from the EcoRI site lies the start of the thiolase structural gene, assigned by comparing the DNA sequence to the NH$_2$-terminal amino acid sequence. The NH$_2$-terminal sequence lies in the single long open reading frame which extends from position −89 to the stop colon (TAG) at nucleotide 1174. Beginning with a serine and extending for 25 residues, the experimentally determined NH$_2$-terminal sequence aligns identically with residues 2 through 26 of the translated DNA sequence. Translation of the DNA sequence was then used to deduce the remaining amino acid sequence from residue 27 to 391 (nucleotides 79 to 1173). Hence, translation of the DNA sequence from the nucleotide 1 to 1173 (in this reading frame) encodes a 391-amino acid polypeptide with a calculated M$_r$ of 40,598. This value is in very good agreement with that of M$_r$=42,000 determined by SDS-polyacrylamide gel electrophoresis.

Two additional pieces of evidence confirm that this translation produce is the correct amino acid sequence of thiolase. First, a search of the predicted amino acid sequence for the active site peptide (NH2-Gly-Met-Asn-Gln-Leu-Cys-Gly-Ser-Gly-COOH) located this peptide at residues 84–92. Finally, the predicted amino acid composition from the translation product and that determined experimentally are in excellent agreement. The G/C content of the 1.46 kb EcoRI-SalI fragment is high, 66.2%. When considered separately, the 5'-flanking 290 bp has a G/C content of 57.4% and the structural gene region 68.4%. The amino acid sequence confirms that the Z. ramigera thiolase contains 5 cysteine residues. The Z. ramigera active site cysteine is at residue Cys-89. Additional cysteines which may be involved in inter- or intradisulphide bonds are Cys-125, Cys-323, Cys-377 and Cys-387. $NH_2$-terminal sequence analysis indicated a serine at position 1.

Seven nucleotides upstream from the ATG start codon is a potential ribosome-binding site, 5'-CTGAGGA-3', identified by homology to the E. coli sequence. Additional start codons including two GTGs which can initiate translation in some bacterial genes are located further upstream. Examination of the 5'-flanking region for homology to the "−10" and "−35" E. coli promoter elements, identified a potential "−35' region at residues −122 to −116 and a corresponding "−10 region", 5'-TATAAT-3', at position −100 to −95. A poly (T) tract at position −255 to −266 is also present. It is clear that the only post-translational processing of thiolase is the removal of the N-formylmethionine residue, as alternate start codons, ATC or GTG, are either out of frame or have an in-frame stop codon before the start of the structural gene.

The 1.5 Kb SalI-EcoRI fragment from pUCDBK1 contains the entire Z. ramigera thiolase structural gene plus 283 bp of 5'/flanking DNA. A series of plasmid constructions were made in which this DNA fragment was inserted into the tac promoter vector pKK223-3 (or derivatives thereof). pZT3 was made by cleaving pUCDBK1 with SalI, blunt-ending with Klenow polymerase and adding on EcorI linkers. Following digestion with EcoRI the 1.5 Kb fragment was purified from an agarose gel and inserted into the EcoRI site of pKK223-3. Recombinant clones having the gene inserted in the correct orientation with respect to the tac promoter were identified by restriction analysis following transformation of E. coli JM105.

A series of clones deleted of sequences in the 283 by flanking the 5' end of the thiolase gene was then constructed. pUCDBK1 DNA was digested with EcoRI and treated with Bal31 nuclease. Following SalI digestion, the ends of the fragments were repaired with Klenow and EcoRI linkers added on. The plasmid DNA was cleaved with EcoRI and fragments in the correct size range, 1.2–1.4 kb, purified from an agarose gel and ligated into the EcoRI site of PKK223-3. Clones of interest were identified by restriction mapping and the extent of the 5'-deletion determined by DNA sequencing. From this series of clones, pZT3.1–pZT3.5, the clone with the largest deletion, pZT3.5, had 84 bp of the 5'-flanking DNA remaining and therefore a subsequent Bal31 deletion experiment was carried out as follows: pZT3.5 DNA was digested to completion with EcoRI and treated with a Bal31 nuclease; the ends were repaired using Klenow polymerase acid EcoRI linkers ligated on, following digestion to completion with EcoRI and BamHl, fragments corresponding to the $NH_2$-terminal region of thiolase were eluted from an agarose gel, ligated with BamHl-EcoRI digested M13mp 11 DNA and plated out on E. coli JM101; single-stranded DNA was prepared from 50 transformants and the extent of the 5'-deletion analyzed by T-tracking; double-stranded DNA was prepared, in vitro from clones of interest and the EcoRI-BamI inserts recovered by restriction digestion and elution from an agarose gel.

In order to reconstruct the intact thiolase gene, the 290 bp BamHl-HindIII fragment from pZT3.5 was ligated into a vector (pKK226) derived from pKK223-3 by deleting the BamHl site upstream from the tac promoter; this C-terminal vector was subsequently used for the reconstruction of the bal31 deleted $NH_2$-termini of interest; clones pZT3.5.1 and pZT3.5.2 were used in subsequent studies.

The effect of deleting sequences in the 283 bp of DNA flanking the thiolase ATG translation initiation codon was determined by analyzing the level of thiolase activity produced by plasmids pZT3.1–pZT3.5.2. 100 ml cultures of the E. coli JM105 containing each plasmid were induced with IPTG for 15 hours and the level of thiolase assayed. The most notable feature of these results is the very high level of thiolase expression obtained with clones pZT3.3–pZT3.5.2, the maximum obtained being 178 U/mg for pZT3.5. This represents an increase of 5.9-fold as compared to plasmid pZT3 which contains the entire 283 bp of 5'-flanking DNA. The data demonstrate that the thiolase 5'-flanking sequences located between −84 (pZT3.5) and −168 (pZT3.2) strongly inhibit the expression of the thiolase gene from the tac promoter. The location of these sequences can be narrowed down to the region between −84 (pZT3.5) and −124 (pZT3.4) as the deletion of this region results in the maximum level of tac-directed thiolase expression. Further deletions to −37 (pZT3.5.1) and −26 (pZT3.5.2) do not increase the level of thiolase expression, and in fact a slight decrease is observed. It is important to note that the time course of induction for this series of clones follows the same kinetics as pZT3 and is not appreciably affected by the deletions.

In order to determine if the thiolase promoter lies in the region −84 (pZT3.5) to −124 (pZT3.4), S1 nuclease protection experiments were carried out according to the method of Berk and Sharp, Cell 12, 721–732 (1977) on Z. ramigera RNA. Total RNA was isolated from a 100 ml mid-log phase culture by the hot phenol/glass beads extraction procedure of Hinnenbusch et al., J. Biol. Chem. 258, 5238–5247 (1983). $5'$-$^{32}$P-labelled DNA probe was prepared as follows: 10 μg, plasmid pZT3.1 DNA was digested to completion with AvaI subsequently treated with CIP; the AvaI restriction fragments were labelled at the 5'-end with [gamma-$^{32}$P]-ATP and polynucleotide kinase; following EcoRI digestion, the DNA was separated on an 8% acrylamide gel and the $^{32}$P-labelled 280 bp probe fragment eluted and recovered by ethanol precipitation. Probe (10,000 cpm) and 11 μg RNA were pooled, freeze dried, resuspended in 10 μg hybridization buffer (40 mM pipes, pH 6.4; 1 mM EDTA, pH 8.0; 0.4 M NaCl; 80% (v/v) formamide), denatured for 10 min at 90° C. and annealed at 55° C. overnight. 235 microliters ice-cold S1 nuclease buffer (0.25 M NaCl; 30 mM NaOAc; 1 mM $ZnSO_4$; 200 μg single stranded calf thymus DNA) containing 2000 units of S1-nuclease was added followed by an incubation at 37° C. for 30 min. The reaction mixture was extracted once with phenol-chloroform and ethanol precipitated in the presence of 0.2 M NaOAc and 10 μg yeast tRNA carrier. The resulting fragments were analyzed on a 6% (w/v) acrylamide, 7 M urea DNA sequencing gel. For size standards, the Maxam Gilbert G and C sequencing reactions were performed on 50,000 cpm of $5'$-$^{32}$P-labeled probe DNA. The results clearly show a protected fragment and that the RNA start site is located at the C or T residue, position −86 or −87. A control indicates that in the absence of Z. ramigera RNA, the probe is completely degraded, demonstrating the presence of the thiolase promoter regions approximately 10 bp (−96) and 35 bp (−121) upstream. The 5'-untranslated region of the thiolase is 86 bp long.

From the results of the induction experiments, it is clear that the thiolase gene can be expressed at high levels in a soluble, catalytically active form in E. coli. S1-nuclease studies map the transcription start site for the thiolase gene in Z. ramigera at nucleotides −86/−87.

Studies have demonstrated that although the "−35" region of the thiolase promoter is recognized and binds the RNA polymerase, it is the "−10" region which determines the rate of transcription initiation. In the case of pZT3, for example, the simultaneous binding of an RNA polymerase molecule to both the bector and insert promoters would result in the rapid initiation of transcription from the tac promoter which would subsequently be impeded by the presence of the polymerase molecule bound at the Zoogloea promoter. The closer the two promoters are linked, the less chance of polymerase binding to both at the same time and the lower the inhibition. Therefore, this represents one means for controlling rate of expression of the enzyme.

Identification of the Z. ramigera Reductase Gene

After identifying the promoter region of the thiolase gene and noting the absence of any potential terminator sequences downstream from the thiolase TAG stop codon, the remaining 2 kb of Zoogloea DNA present in clone pUCDBKl was sequenced and examined for the reductase gene. A series of expression plasmids (pZT1–pZT3) containing either the entire pUDCBKl insert or fragments thereof were constructed in the E. coli tac promoter vector pKK223.3. Each plasmid has the thiolase gene located in the correct orientation for expression from the tac promoter. It is reasonable to expect the tac promoter to direct not only thiolase expression but the expression of any genes located in the 2.3 kb downstream in an operon-like type organization. Clone pZT1 was constructed by inserting the entire 3.8 kb EcgRl Z. ramigera DNA insert from pUCDBKl into the EcoRl site of the vector pKK223-3. Subsequently, pZT2 was derived from pZT1 in a straightforward manner by deleting the 850 bp SmaI fragment. pZT3 is constructed as described for the identification of the thiolase promoter. A series of tac promoter induction experiments were performed on each of the recombinant clones pZt1, pZT2 and pZT3. The vector pKK223-3 was used as a control.

E. coli cells, containing each of the plasmids were grown and induced by the addition of isopropyl-beta-D-galactopyranoside (IPTG) to a final concentration of 2 mM. After 15 h induction, 10 ml cultures were harvested and lysed by sonication. The cell lysates from each clone were then analyzed both by enzyme assay and on SDS-PAGE. No PHB polymerase activity was detected in any of these lysates. Each of the three recombinant plasmids pZT1, pZT2 and pZT3 demonstrate substantial levels of thiolase activity. In addition, the lysates from pZT1 and pZT2 have comparably high levels of AcAc-CoA reductase activity using NADPH as the cofactor. No reductase activity is detected in any of the lysates when HADH is used as a cofactor. The control, pKK223-3, has neither thiolase nor reductase activities. To confirm that the lysates from pZT1 and pZT2 do in fact contain the correct reductase, these lysates were also assayed for oxidation of D(-)beta-hydroxybutyryl-CoA. In both cases, enzyme activity was observed with NADP as electron acceptor.

Each of the lysates described above was also analyzed by SDS-PAGE. The results show the presence of the thiolase protein at around 42,000 daltons in protein lysates from pZT1, pZT2 and pZT3, which is not present in the control, pKK223-3. Lysates of pZT1 and pZT2 also have a small, 25,000 dalton protein which is not present in the lysate of pZT3 or the control, which corresponds to the AcAc-CoA reductase. The results demonstrate that the AcAc-CoA reductase gene is located downstream from the thiolase gene. The entire structural gene for this enzyme must be located between the 3'-end of the thiolase and the first SmaI site downstream in pUCDBKl.

Identification of the Translation Start Site and Overexpression of the Reductase Gene The complete nucleotide sequence of the 2339 bp located 2.3 kb downstream from the first SalI site in pUCDHKl is shown in FIG. 2. Computer analysis of the sequence data, using codon usage information from the thiolase gene as a standard, identified three open reading frames. N-terminal protein sequence data was obtained from the 25,000 dalton band present in induced lysates from pZT1 and pZT2 following preparative SDS-PAGE and electroelution. This data was used to confirm the translation start site for the corresponding gene. The N-terminal five amino acids determined experimentally match residues 2 through 6 predicted from the DNA sequence of the first open reading frame. Translation of this reading frame predicts a polypeptide of 25,000 molecular weight. The translation product of the first open reading frame starting at the ATG, nucleotide 37 and ending at the 758 before the TGA stop codon nucleotide is shown in FIG. 2. This is the predicted primary amino acid sequence of the acetoacetyl-CoA reductase protein.

It is evident that the acetoacetyl-CoA reductase gene in clones pZT1 and pZT2 can be expressed at reasonably high levels in E. coli. However, in both of these cases, the expression of the reductase gene from the tac promoter is not optimum due to the presence of the thiolase structural gene and 5'-flanking sequence. A simpler acetoacetyl-CoA reductase overproduction vector, pZR14, was constructed. pUCD-BKl DNA was digested to completion with SalI and SmaI and the SalI ends repaired using the Klenow fragment of DNA polymerase. Following the addition of EcoRl linkers and digestion with EcoRl, the fragments were separated by agarose gel electrophoresis. The 1.05 kb fragment corresponding to the acetoacetyl-CoA reductase structural gene plus 36 bp flanking the 5'-end and 266 bp flanking the 3' end was purified and ligated into the. EcoRl site of pKK223-3. pZR14 was then identified as having the correct restriction map with the reductase gene in the right orientation. Induction experiments were performed on pZR14 as described for pZT1, pZT2 and pZT3. Acetoacetyl-CoA reductase was expressed.

Identification of the Thiolase and Reductase Genes in A. eutrophus

The methods used in isolating the first two PHB genes from Zooloea were applied to the identification, isolation and characterization of gene from another PHB producing species, Alcaligenes eutrophus, using the Zooloea thiolase gene region as a hybridization probe to locate homologous sequences.

Subsequent sequence analysis of a 2 kb Pst1 fragment of A. eutrophus DNA cloned into pUC8 (clone pAeT3) identified the corresponding thiolase gene region in the A. eutrophus H16 genome. The downstream sequences in pAeT3 are also homologous to the NADP-linked reductase gene region from the Zoogloea clone PUCDBKl. The sequences of the Alcaligenes thiolase and reductase genes is shown in FIG. 3.

Cloning of the individual thiolase and reductase genes from pAeT3 into pKK 223.3, leads to expression of the corresponding enzymes. Comparisons of the Zoogloea and A. eutrophus thiolase protein sequences establish that the two proteins are 63% homologous, including the active site Cys-89.

Both the *A. eutrophus* and *Zoogloea* thiolase gene regions were used as hybridization probes to screen *Nocardia* and *Pseudomonas olevarans* DNA for homologous genes. Techniques for identifying the thiolase, reductase, and other synthetase genes from other species having homologous sequences in addition to those described above, are known to those skilled in the art.

Identification of the *Z. ramigera* PHB Polymerase Gene

PHB polymerase from *Z. ramiaera* utilizes D(-)-hydroxybutyryl-CoA monomers, polymerizing them in oxoester linkages in a template-independent head to tail condensation to yield linear polymers. These polymers can contain up to 10,000 monomer units with a molecular weight in excess of $1 \times 10^6$. The polymer rapidly becomes insoluble and accumulates as discrete granules in the cell.

As described in U.S. Ser. No. 067,695 filed Jun. 29, 1987, a conjugal transfer system based on derivatives of the broad host range plasmid pRK290, described by Ditta et al., in *Proc. Natl. Acad. Sci. USA* 77, 7347–7351 (1980), transposon mutagenesis and complementation analysis can be used in conjunction with the isolation, characterization and complementation of PHB negative mutants to isolate the PHB polymerase gene for *Z. ramigera* and *A. eutrophus*. As described by Schlegel et al., *Arch. Microbiol.* 71, 283–294 (1970), sudan-black staining is used for the detection of PHB negative mutants. Complementation of the mutants is screened for by growing, harvesting and lysing the cells to release PHB that can then be purified to determine its presence and molecular weight distribution. Thiolase, reductase and PHB polymerase activities in the lysates are also assayed.

Identification of the *A. eutrophus* PHB Polymerase Gene

These techniques were also applied to the cloning, sequencing and expression of the PHB polymerase gene (phbC) in *Alcaligenes eutrophus* H16 using complementation of poly(B)-hydroxybutyrate-negative mutants of: *A. eutrophus* H16. The results demonstrate that the genes encoding the three enzyme of the PHB biosynthetic pathway are organized phbC-phbA-phbB. Expression of all three genes in *E. coli* results in a significant level (50% dry cell weight) of PHB production in this bacteria. phbC encodes a polypeptide of Mr=63,900 which has a hydropathy profile distinct from typical membrane proteins indicating that PHB biosynthesis probably does not involve a membrane complex.

The strategy of constructing, characterizing an complementing PHB-negative mutants of a derivative (11599 Sl, Table 1) of *A. eutrophus* H16 was used to identify and isolate the gene(s) encoding PHB polymerase. Transposon mutagenesis allowed use of DNA hybridization analysis to map the chromosomal location of the Tn5 insertion in any interesting strains. 32 potential PHB negative mutants were identified by their opaque colony phenotype when grown on nitrogen limited minimal agar plates. Due to the procedure used to enrich for PHB-deficient strains, it was not surprising that the 32 mutants were found by DNA hybridization using a Tn5 DNA probe to belong to only three classes. More detailed DNA hybridization studies were then used to analyze a representative from each class, i.e., strains PHB #2, PHB #3 and PHB #19. From these studies, it was possible to conclude that in the case of strain PHB #2 and strain PHB #3, the Tn5 insertion causing the opaque phenotype was located in the chromosome approximately 1.2 kb and 1.6 kb, respectively, upstream from the phbA-phbB genes, as illustrated on FIG. 3. For strain PHB #19, the Tn5 insertion was located elsewhere on the *A. eutrophus* chromosome.

The experimental procedure and materials used in the isolation and characterization of phbC were as follows. The procedures and materials are similar to those described for isolation of the phbA and phbB genes.

Bacterial strains and plasmids are shown in Table 1. Media and culture conditions are as described above.

TABLE 1

Bacterial Strains and Plasmids.

| Strain | Relevant Characteristics | Reference |
|---|---|---|
| *E. coli* | | |
| JM83 | | |
| DH5α | Host strain for plasmids | BRL |
| *A. eutrophus* | | |
| H16 | Wild type strain | ATCC17699 |
| 11599 | — | NCIB 11599 |
| 11599S1 | Strep$^r$ | |
| PHB#2 | H16[phb2::Tn5] | |
| PHB#3 | H16[phb3::Tn5] | |
| PHB#19 | H16[phb19::Tn5] | |
| Plasmids | | |
| pAeT29 | phbA-phbB | |
| pAeT10 | phbA-phbB | |
| pLAFR3 | Tc$^r$, cosmid vector | B. Staskawicz |
| pRK2013 | Nm$^r$ | |
| pRK602 | Cm$^r$, Nm$^r$, pRK2013 nm::Tn9 containing Tn5 | |
| pUC18 | Ap$^r$ | |
| pUC19 | Ap$^r$ | |

DNA manipulations were similar to those described above. Restriction endonucleases, T4 DNA ligase and DNA polymerase 1 were obtained from New England Biolabs and used as directed by the manufacturer. Calf intestinal alkaline phosphatase was purchased from Boehringer Mannheim Corporation. All routine DNA manipulations, including plasmid purifications, *E. coli* transformations, etc. were performed using methods described by Maniatis, et al. Chromosomal DNA was purified from *A. eutrophus* strains, grown to late logarithmic phase in TSB as described previously. Transfer of restriction digested DNA samples from agarose gels to nitrocellulose filters, prehybridization and hybridization with $^{32}$P-labelled DNA probes was as previously described. Rapid plasmid isolation from *A. eutrophus* recombinant strains, for restriction analysis, was performed by the alkaline extraction procedure.

Conjugation in *A. eutrophus*

The conjugal transfer of the broad host range plasmid, pLAFR3, or recombinant derivatives of pLAFR3, into *A. eutrophus* was performed using the same method as previously described. In this case, however, the recipient *A. eutrophus* cells were not sonicated and transconjugants were selected on *A. eutrophus* mineral agar plates containing 0.01% NH$_4$Cl as nitrogen source, 1% (w/v) fructose as carbon source and 10 μg/ml tetracycline.

For Tn5 mutagenesis, a spontaneous streptomycin resistant strain of *A. eutrophus* 11599 (1599 S1) was used. Transfer of pRK602 (Tn5) was carried out as described above using *E. coli* MM294A (pRK602) as the only donor. *A. eutrophus* strains containing Tn5 were selected for by growth on streptomycin (500 μg/ml) and kanamycin (100 μg/ml).

Amplification and Identification of PHB-Deficient Mutants

The amplification and screening procedures described by Schlegel and Oeding, *Radiation and Radiosotopes for Industrial Microorganisms*. International Atomic Energy Agency, Vienna, 223–231 (1971) was used to identify PHB-deficient strains of A. eutrophus. A pool of around $10^5$ Kan$^r$ transconjugants (Tn5 insertion mutants) was inoculated into 10 ml of mineral media containing 0.01% NH$_4$Cl, 1% fructose and 100 μg/ml kanamycin and incubated for 18 h at 30° C. This culture was then used to inoculate 100 ml of the same medium and incubated for 30 h at 30° C. To amplify PHB-deficient mutants, aliquots of this culture containing approximately $10^9$ cells were fractionated on sucrose step gradients by density equilibrium centrifugation and plated out on mineral agar plates containing 0.01% NH$_4$Cl, 1% fructose and 100 μg/ml kanamycin. After growth for 4–5 days at 30° C., opaque (PHB-deficient) and white (PHB-containing) colonies were readily distinguished. By quantitating the level of PHB produced by both opaque and white colonies, it was confirmed that opaque colonies were PHB-deficient whereas white colonies contained PHB.

Analysis of Proteins

In order to perform assays for β-ketothiolase, NADPH-linked acetoacetyl-CoA reductase and PHB-polymerase, 100 ml cultures of A. eutrophus strains were grown at 30° C. for 40 hours in TSB. For Tn5 mutant strains, kanamycin was added at 100 μg/ml and for strains containing pLAFR3 or derivatives thereof, tetracycline was added to 10 μg/ml. Cells were harvested by centrifugation, resuspended in 2 ml lysis buffer (10 mM Tris HCl, pH 8.0; 5 mM β-mercaptoethanol; 5 mM EDTA, 0.02 mM phenyl-methyl-sulfonyl-fluoride; 10% v/v glycerol) and lysed by sonication. An aliquot of the lysate was cleared of cell debris by centrifugation for β-ketothiolase and acetoacetyl-CoA reductase assays. β-ketothiolase activity was determined by measuring the rate of thiolysis of acetoacetyl-CoA as described by Davis, et al., J. Biol. Chem. 262, 82–89 (1987), of acetoacetyl-CoA with NADPH as the cofactor. PHB polymerase assays were performed using samples of the crude lysate and determining the level of incorporation of D-$^3$H-hydroxybutyryl-CoA (specific activity approximately 2 μCi/μmol), as described by Fukui, et al., Arch. Microbiol. 110, 149–156 (1976). Protein concentrations were determined by the method of Bradford, Anal. Biochem. 72, 248–254 (1976), using Biorad assay solution and bovine serum albumin as the standard. E. coli maxi-cell labelling studies were performed as described by Sancar, et al., J.Bacteriol, 137, 692–693 (1979).

PHB Purification and Quantitation

To determine the level of PHB in different strains, 100 μl aliquots of the crude lysates were treated with 1.2 ml of 5% Na hypochlorite solution for 1 h at 37° C. The insoluble PHB was then harvested by centrifugation for 10 min in a microcentrifuge, washed successively with 1 ml of H$_2$O, 1 ml acetone, 1 ml of ethanol and dried under vacuum. PHB concentrations were then determined spectrophotometrically as described by Law and Slepecky, J.Bacteriol. 82, 33–36 (1961) using a standard curve and expressed as mg PHB/mg protein.

Plasmid Constructions and Complementation Analysis

Plasmids pLA29, pLA40, pLA41 and pLA42 were constructed by cloning restriction fragments of the pAeT29 insert into the broad host range vector pLAFR3 for complementation analysis of the PHB-negative A. eutrophus strains, pLAFR3 is a derivative of pLAFR1, described by Friedman, et al., Gene 18, 289–296 (1982), containing a pUC8 polylinker cloning site inserted into the EcoR1 site. Different fragments of pAeT9 were cloned into pLAFR3, pLA29 was constructed by ligating the entire 15 kb EcoR1 insert from pAeT29 into the EcoR1 site of pLAFR3. To facilitate the construction of pLA40, pLA41 and pLA42, the corresponding fragments were first cloned into pUC18 to produce plasmids pAeT40, pAeT41 and pAeT42. The fragments were then excised by digestion with BamHI and EcoR1 from the pUC18 plasmids, purified following agarose gel electrophoresis and ligated into BamH1/HindIII digested pLAFR3. T construct pAeT40, pAeT29 DNA was digested to completion with Ndel and the cohesive ends filled in using the Klenow fragment of DNA polymerase. After separating the fragments on an agarose gel, the 7 kb fragment of interest was purified by electroelution, ligated into the Smal site of pUC18 and the recombinant plasmid pAeT40 subsequently identified by restriction analysis after transforming E. coli DH5α cells. This construction eliminates the acetoacetyl-CoA reductase activity since on the Ndel sites is located within the structural gene for this enzyme. For the construction of pAeT41, Smal/EcoR1 digested pAeT29 DNA was separated on an agarose gel and the 5 kb Smal/EcoR1 fragment purified and ligated into Smal/EcoR1 digested pUC18 to give the correct plasmid. Deletion of the 2.3 kb Pst1 fragment containing the β-ketothiolase and acetoacetyl-CoA reductase structural genes by partial Pst1 digestion of pAeT41 DNA and religation was used to construct pAeT42.

Hybridization Mapping of Tn5 Insertions

A library of $10^5$ individual Tn5 insertion mutants of A. eutrophus 11599 S1 was constructed and 32 potentially PHB-negative colonies, identified by their opaque colony phenotype on nitrogen limited minimal plates, as described above. These were further characterized using Southern DNA hybridization analysis. For the DNA hybridization studies restriction digested chromosomal DNA from each strain was analyzed using both a Tn5 DNA probe (plasmid pRK602) and two plasmids, pAeT10 and pAeT29 which contain the A. eutrophus phbA-phbB locus (FIG. 3).

The 32 "opaque" strains represented multiple copies of only three distinct mutant types. These three distinct mutant types are represented by strains PHB #2, PHB #3 and PHB #19. For strains PHB #2 and PHB #3, the transposon TN5 is inserted into chromosomal Pst1 fragments of 2.3 kb and 0.6 kb, respectively. Both of these chromosomal Pst1 fragments are located on the 15 kb of A. eutrophus DNA cloned in plasmid pAeT29, but not in the phbA-phbB structural genes. Strain PHB #19 has Tn5 inserted into a Pst1 fragment, not present on the pAeT29 plasmid.

More detailed DNA hybridization experiments were performed on the chromosomal DNA from strain PHB #2 and strain PHB #3 to map the site of the Tn5 insertion in each of these mutants. Chromosomal DNA from each of these strains as well as the wild type strain H16 and strain PHB #19 was digested with Sal1, Sma1 and BglII, transferred bidirectionally to nitrocellulose filters and hybridized with Tn5 DNA (pRK602) and pAeT29 DNA probes to map the location of the Tn5 insertions in strains PHB #2 and PHB #3.

The results of a biochemical analysis of wild type H16 and each of the mutuant strains PHB #2, PHB #3, and PHB #19 is presented in Table 2. 100 ml stationary phase cultures of each strain were harvested, lysed and assayed for PHB content and β-ketothiolase, NADP-specific acetoacetyl-CoA reductase and PHB polymerase activities. Under these growth conditions wild type H16 produces a significant level of PHB (1.3 mg PHB/mg protein, Table 2) and has a high level of all three enzyme activities. Mutant strains PHB #2 and PHB #3 produce essentially no PHB and strain PHB #19 produces only 5% of the wild type level (Table 2). PHB polymerase activity could not be detected in any of these mutant strains, however, the presence of PHB in the lysate of strain PHB #19 indicates that the enzyme is there although the activity is probably below the detection level of the assay. β-ketothiolase activities in all three mutants are reduced to the order of 45% (PHB #2) to 38% (PHB #19) that of wild type strain H16. Similarly, NADP-specific acetoacetyl-CoA reductase activities are around 50% of the wild type level. It was concluded from these data that the PHB-polymerase gene was located upstream from phbA-phbB and that the expression of the latter genes is affected by the Tn5 insertion upstream in the case of strains PHB #2 and PHB #3.

A series of plasmids containing fragments of the *A. eutrophus* insert of plasmid pAeT29 were constructed in the broad host range vector pLAFR3 for complementation analysis of the PHB-negative mutants.

Each of the recombinant plasmids, pLA29, pLA40, pLA41 and pLA42 were introduced into each of the *A. eutrophus* strains by conjugation and the resulting transconjugants analyzed on nitrogen limited plates for the restoration of the white (PHB plus) phenotype. Plasmids pLA29, pAL40, pLA41 and pLA42, each of which contains the region upstream from phbA-phbB into which Tn5 has inserted in the chromosome of strains PHB #2 and PHB #3, complemented the mutation in each of these two strains, restoring the white colony phenotype. All four recombinant plasmids also restored the wild type colony phenotype to mutant strain PHB #19. In the case of these strain, the Tn5 insertion is located outside the region of the *A. eutrophus* chromosome contained in each of the plasmids. Control experiments using the vector pLAFR3 resulted in the opaque colony phenotype when introduced into each of the three mutant strains.

Biochemical analysis of each of the complemented strains was performed as described for the characterization of the mutants and these results are also presented in Table 2. The introduction of pLA29 into each of the mutant strains results in the restoration of PHB polymerase activity and PHB biosynthesis (Table 2). In addition, an approximately three to five-fold increase in the levels of β-ketothiolase and NADP-specific acetoacetyl-CoA reductase activities was observed. Plasmid pLA40 and pLA41 also restore PHB-polymerase and PHB production to strains PHB #2 (Table 2), PHB #3 and PHB #19, although in the case of the pLA40, the phbB gene was disrupted during the construction of this plasmid. Finally, plasmid pLA42 restores PHB polymerase activity and PHB production to all three mutant strains although the phbA-phbB genes have been deleted. In the case of strains containing this plasmid the β-ketothiolase and NADP-specific acetoacetyl-CoA reductase activities remain at the same level as the mutant strains (Table 2).

TABLE 2

Biochemical analysis of mutant and complemented *A. eutrophus* H16 strains.

| Strain | PHB[1] | Thiolase[2] | Reductase[2] | Polymerase[3] (×10³) |
|---|---|---|---|---|
| H16 | 1.3 | 8.9 | 1.0 | 3.9 |
| PHB#2 | <0.01 | 4.0 | 0.5 | ND |
| PHB#3 | <0.01 | 3.4 | 0.5 | ND |
| Tn5#19 | 0.6 | 3.2 | 0.4 | ND |
| H16/pLA29 | 1.0 | 28.7 | 9.2 | 5.3 |
| PHB#2/pLA29 | 1.5 | 27.5 | 3.5 | 3.8 |
| PHB#3/pLA29 | 0.9 | 24.8 | 4.4 | 0.7 |
| PHB#19/pLA29 | 1.8 | 26.7 | 4.9 | 1.0 |
| PHB#2/pLA40 | 0.9 | 20.4 | 0.45 | 0.6 |
| PHB#2/pLA41 | | 18.0 | 3.7 | 0.9 |
| PHB#2/pLA42 | 1.2 | 2.0 | 0.3 | 4.3 |

TABLE 2-continued

Biochemical analysis of mutant and complemented *A. eutrophus* H16 strains.

| Strain | PHB[1] | Thiolase[2] | Reductase[2] | Polymerase[3] (×10³) |
|---|---|---|---|---|
| PHB#3/pLA42 | 0.9 | 5.5 | 0.5 | 0.6 |
| PHB#19/pLA42 | 1.2 | 5.5 | 0.4 | 0.6 |

[1]mg/mg of protein
[2]units/mg of protein
[3]cpm/min/mg of protein
ND: no detectable activity
Results shown are the average of two or more experiments.

As described above, the phbA-phbB genes located on plasmid pAeT29 were expressed in *E. coli* under the control of the *A. etrophus* promoter. Identification of the phbC gene upstream from phbA-phbB together with the observed decrease in thiolase and reductase enzyme activities in strains PHB #2 and PHB #3 indicates that all three genes are expressed from a single promoter located upstream from phbC. To study this, cultures of *E. coli* strains containing plasmids pAeT41 and pAeT42 were grown under nitrogen limiting conditions until cells reached stationary phase at which point the cells were harvested, lysed and analyzed. *E. coli* containing pUC18 was used as a control. The results of β-ketothiolase, acetoacetyl-CoA reductase, PHB polymerase and PHB concentration assays, shown in Table 3, indicate that the lysate of *E. coli* containing plasmid pAeT41 has a significant level of each enzyme activity and PHB production.

Maxi-cell analysis of the *E. coli* strains described above was used to determine the molecular weight of the polypeptides encoded by plasmids pAeT41 and pAeT42. Plasmid pAeT10 was included in the analysis as this plasmid expresses the *A. eutrophus* phbA-phbB genes from the pUC8 vector lacZ promoter. Additional protein bands are present of Mr 40,000 and Mr 26,000 in lanes 1 and 2 containing plasmid pAeT10 and pAeT41, respectively. Both of these plasmids express the phbA-phbB genes encoding β-ketothiolase (Mr 41,000) and NADP-specific acetoacetyl-CoA reductase (Mr 26,000). Neither of these two proteins is present in the extract of cells containing plasmid pAeT42 (lane 3) which does not contain the phbA-phbB genes. Control experiments in which the vector pUC8 was used gave no signal at Mr 41,000 or Mr 26,000. Both plasmids, pAeT41 and pAeT42, express the PHB polymerase (phbC) gene in *E. coli,* and in lanes 2 and 3 which contain extracts of cells containing these plasmids a signal at $M_r$ 58,000 is clearly evident. Again, this protein is absent from lane 1 which contains the extract from cells containing plasmid pAeT10 which does not contain the phbC gene and also from a control sample of PUC8 containing cells. An additional band of around Mr 30,000 is present in all 3 lanes and was also found in control experiments of cell extracts containing pUC8 and is presumably a vector protein. From these data we conclude that the phbC gene expressed in *E. coli* encodes a polypeptide of approximately $M_r$ 58,000.

TABLE 3

Biochemical analysis of recombinant *E. coli* strains to determine expression of phbC-A-B in *E. coli*.

| Plasmid | Thiolase U/mg Protein | Reductase U/mg Protein | Polymerase cpm/min/mg Protein | PHB mg/mg Protein |
|---|---|---|---|---|
| pUC18 | 0.5 | ND | ND | 0.015 |
| pAeT41 | 59.0 | 2.5 | $2.4 \times 10^4$ | 2.977 |
| pAeT42 | 0.9 | ND | $0.02 \times 10^4$ | 0.011 |

ND: no detectable activity
Results shown are the average of two or more experiments.

Nucleotide Sequence Analysis of phbC

The 2 kb Smal-Pst1 *A. eutrophus* chromosomal DNA fragment cloned in plasmid pAeT42 contains the entire structural gene for phbC and probably the regulatory sequences. This fragment was sequenced from both DNA strands multiple times using the dideoxy sequencing method as described above. A single long open reading frame extends from nucleotide 820 to a TGA stop codon at nucleotide 2608. Potential translation initiation condons are present at position 842 (ATG), 1067 (ATG) and 1097 (ATG). Translation from each of these potential start sites would produce proteins of Mr 63,940, Mr 55,513 and Mr 54,483, respectively. Significant amino acid sequence homology between the translation product from the ATG at position 842 to the ATG at position 1067 and the *P. oleovarans* PHA polymerase gene product, described below, indicates that the first ATG (position 842) is probably correct. FIG. 4 represents the entire nucleotide sequence of this region from the Sma1 site to the first 30 nucleotides of the phbA gene located downstream. The translation product of the open reading frame from the ATG at position 842 to the TGA at position 2609 is also shown. The PHB polymerase encoded by the phbC gene in plasmid pAeT42 is a polypeptide of 589 amino acids with an Mr=63,940. The N-terminal 10 amino acids of the phbA gene product are also presented in FIG. 4. Additional features of the nucleotide sequence presented in FIG. 4 include the C-terminus of an open reading frame which begins upstream from the Sma1 site and terminates at the TGA stop codon at position 76. Located 85 bp downstream from the phbC TGA stop codon (position 2609) lies the ATG start codon for the phbA structural gene (position 2969). From these data it is clear that the three enzymes of the *A. eutrophus* PHB biosynthetic pathway are encoded by three genes organized as phbC-phbA-phbB as illustrated in FIG. 4.

The expression of phbC alone in *E. coli* produces neither PHB nor significant levels of PHB polymerase activity (plasmid pAeT42). *E. coli* appears incapable of synthesizing D-(−)-hydroxybutyryl-CoA, as substrate for PHB polymerase, in the absence of the *A. eutrophus* phbA-phbB genes. Since the insert of pAeT42 contains both the promoter and structural gene for phbC (plasmid pLA42 complements all PHB-negative mutants, Table 2), it can be concluded that in the absence of available substrate, PHB polymerase is inactive or degraded in *E. coli*.

The nucleotide sequence of the *A. eutrophus* chromosomal DNA insert in plasmid pLA42 encoding PHB polymerase predicts a single polypeptide of Mr 63,940 (FIG. 4). Although PHB polymerase has not previously been purified and characterized, the results of *E. coli* maxi-cell studies indicate a Mr=58,000 for this polypeptide, in reasonable agreement with that predicted from the gene sequence.

For a number of years, it was proposed that the polymerization of (D)-β-hydroxybutyryl-CoA involves a membrane bound polymerase which forms a type of barrier between the aqueous environment of the cytoplasm and the hydrophobic crystalline PHB granules. The hydropathy profile of the PHB polymerase polypeptide does not indicate a typical membrane spanning structure. In addition, NMR studies of native PHB granules in *Methylobacterius* indicate that these granules are in a mobile, as opposed to a highly crystalline solid state. Together these data lend credence to the idea that PHB biosynthesis does not in fact require a complex membrane bound polymerization system. The mechanism for PHB polymerase proposed in the literature involves two partial reactions. The initial acyl-S-enzyme intermediate formation is followed by transfer to a primer acceptor in the second reaction. The predicted primary structure of PHB polymerase has 5 cysteine residues, $Cys_{246}$, $Cys_{319}$, $Cys_{438}$ and $Cys_{459}$.

Identification of the *P. oleovarans* PHA Polyermase Gene

The genes involved in the biosynthesis of polyhydroxyalkanoate (PHA) polyesters in *Pseudomonas oleovarans* were also isolated, as follows.

In 1983, de Smet, et al., *J. Bacteriol.* 154, 870–878, identified a polymer produced by *Pseudomonas oleovarans* TF4-1L (ATCC 29347) as poly-B-hydroxyoctanoate. Subsequent studies showed that *P. oleovarans* could produce a range of PHA biopolymers depending on the carbon source used, i.e., n-alkanes and 1-alkenes (Lageveen, et al., *Appl. Environ. Microbiol.* 54,2924–2932 (1988)) or fatty acids (Brandl, et al., *App. Environ, Microbiol.* 54, 1977–1982 (1988). The pathway appears to involve the conversion of the alkanes/alkenes to the fatty acid which then enters the fatty acid B-oxidation pathway, resulting in the formation of the D isomer of the B-hydroxyacyl-CoA, which is incorporated into the polymer by PHA polymerase. *P. oleovarans* has not been shown to incorporate B-hydroxybutyrate indicating that 1) it does not possess the thiolase/reductase enzymes, or 2) the PHA polymerase cannot use B-hydroxybutyrate as a substrate. The broad range of substrates used by the *P. oleovarans* PHA polymerase make the gene encoding this enzyme particularly interesting for biopolymer engineering of polyesters.

Figure 5:
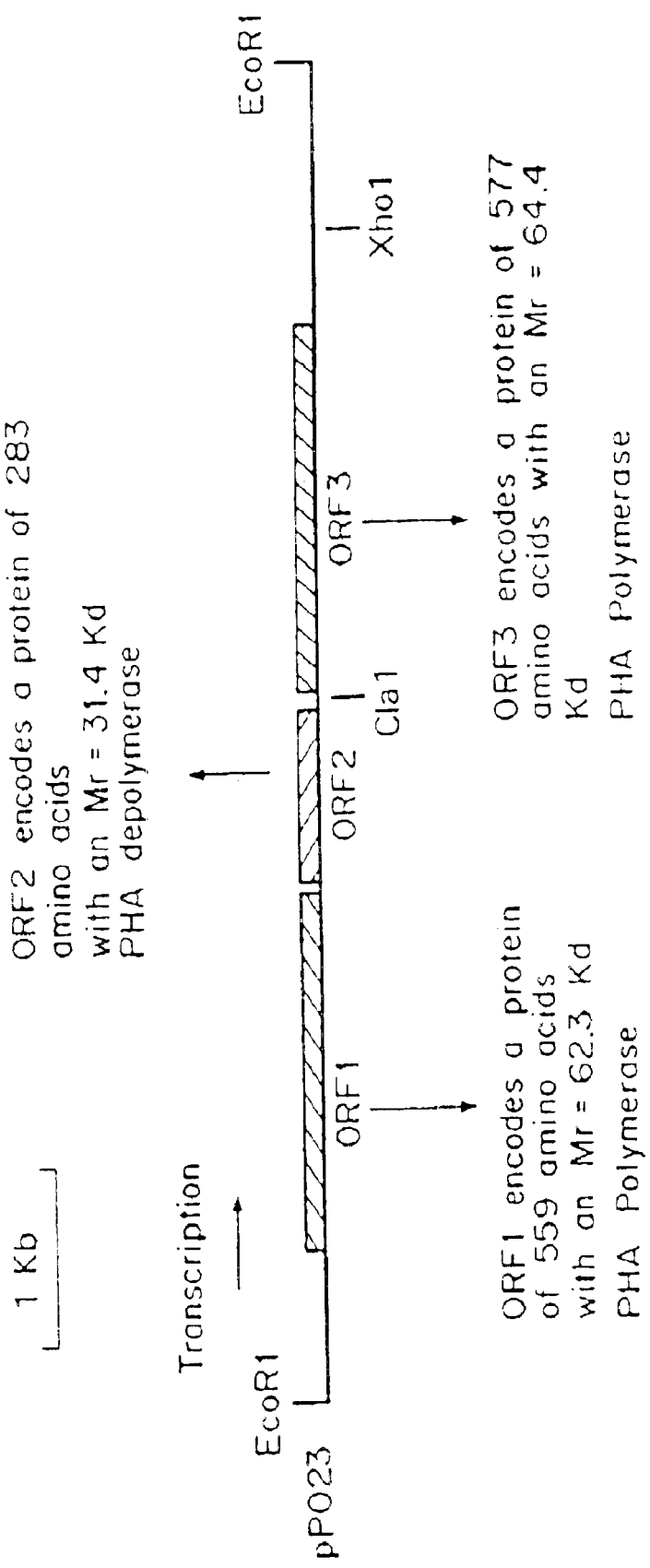
FIG. 5 shows the potential coding regions of the *P. oleovarans* PHA polymerase gene, open reading frames ORF1, ORF2, and ORF3. ORF1 begins at the ATG initiation codon nucleotide 554 and ends at 2230 before the TGA stop codon nucleotides 2231–2233 and encodes a polypeptide of 562 amino acids with an $M_r$=60,000. ORF2 begins at the ATG position 2297 and ends at the TAA position 3146. ORF2 begins at the ATG position 3217 and ends at the TGA position 4948.
Figure 6B:
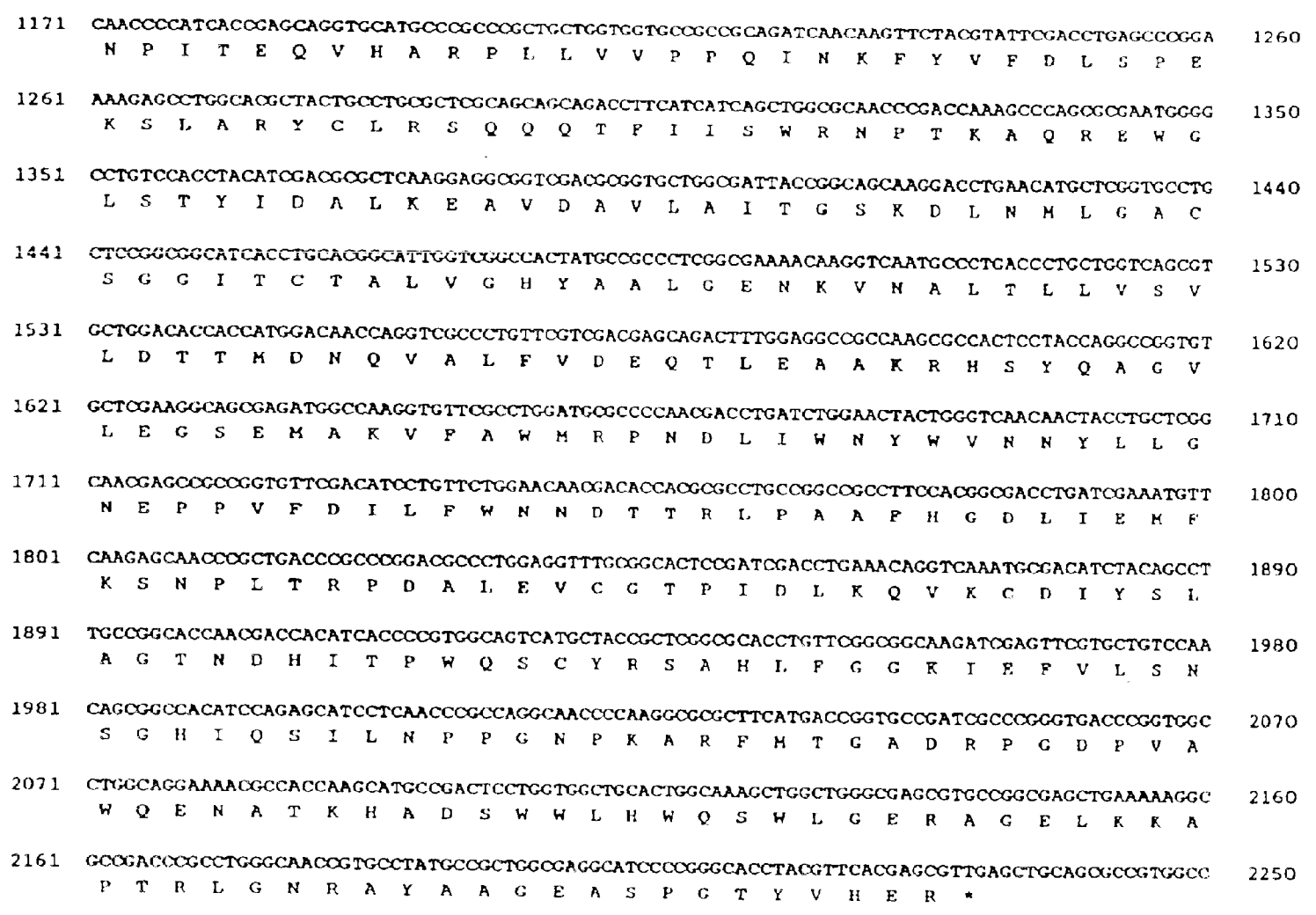

The approach used for isolating the *A. eutrophus* B-ketothiolase and NADP-specific acetoacetyl-CoA reductase using the *Z. ramigera* B-ketothiolase gene as a DNA hybridization probe was followed, as described above, to isolate the *P. oleovarans* PHA polymerase gene. Southern DNA hybridization of *P. oleovarans* chromosomal DNA identified a 6 kb EcoRI restriction fragment with strong homology to the *A. eutrophus* PHB polymerase gene (phbC). The 6 kb EcoRI fragment was cloned in the *E. coli* plasmid vector, pUC18, by standard procedures to give plasmid pPO23. The region which hybridized to the *A. eutrophus* phbC gene is located as indicated in FIG. 5. Nucleotide sequence analysis of the complete 6 kb fragment identified three potential protein coding regions (open reading frames, ORF1, ORF2 and ORF3, indicated on FIG. 5). ORF1 begins at the ATG initiation codon nucleotide 554 and ends at the TGA stop codon nucleotides 2231–2233 (FIG. 6). This open reading frame is contained in the region of the pPO23 insert which hybridizes with the *A. eutrophus* phbC gene. ORF1 encodes a polypeptide of 562 amino acids with an $M_r$=60,000. A comparison of the protein sequence predicted by translation of ORF1 with the amino acid sequence of the *A. eutrophus* PHB polymerase using the program ALIGN revealed 52% identify between the two proteins. These data identify ORF1 as the *P. oleovarans* PHA polymerase gene. ORF3 begins at the ATG position 2297 and ends at the TAA position 3146. ORF2 begins at the ATG position 3217 and ends at 4947 before TGA stop codon at nucleotides 4948–4950. ORF2 and ORF3 are probably co-transcribed with the PHA polymerase gene (ORF1) and are probably proteins involved in PHA biosynthesis.

Synthesis of PHB, PHA and Similar Polymers

It was established above that it is possible to construct new PHB production strains by introducing the A. eutrophus PHB biosynthetic genes into E. coli resulting in the accumulation of up to 50% dry cell weight as PHB. The construction of new or improved polyester production strains is now possible by the expression of either the PHB biosynthetic genes from A. eutrophus or the PHA polymerase gene and ORF2 and ORF3 from P. oleovarans in a number of systems. Plasmids can be constructed which express the A. eutrophus B-ketothiolase and NADP-specific acetoacetyl-CoA reductase genes in P. oleovarans under the control of the xyls promoter in the broad host range expression plasmids pNM185 (Mermod, et al., J.Bacteriol. 167, 447–454 (1986), or pERD20/pERD21 (Ramos, et al., FEBS LETTERS 226, 241–246 (1986). Alternatively, the broad host range tac promoter expression vectors pMMB24/pMMB22 (Bagdasarian, et al, Gene 26, 273–282 (1983)). These same vectors can also be used to express the A. eutrophus PHB polymerase gene or the three P. oleovarans genes cloned in plasmid pP023 (FIG. 5).

Two plasmids, pLAP1 and pLAP2, have been constructed which should express the P. oleovarans PHA polymerase gene and ORF2 (pLAP1) or the PHA polymerase gene and ORF2 plus ORF3 (pLAP2) under the control of the A. eutrophus phbC promoter (FIG. 4).

To construct these plasmids, the 810 bp Sma 1-BstB 1 restriction fragment spanning the first 810 nucleotides of the A. eutrophus insert in plasmid pAeT42 containing the phbC promoter was ligated into the unique Sma 1 site in the E. coli vector pUC19 to obtain plasmid pAeTB1. The P. oleovarans PHA polymerase gene promoter was removed by using the exonuclease Bal31 to delete 170 bp from the end of Fsp1 digested pPO23 DNA and recovering the PHA polymerase structural gene plus ORF2 by subsequently digesting with Cla1 and cloning the fragment into Sma1/Cla1 digest pBLSK+ vector (Stratagene, La Jolla, Calif. 92037). The insert of pPOB10 was identified as containing the last 19 bp upstream from the ATG start codon of the PHA polymerase structural gene (nucleotide 535, FIG. 6) the complete PHA polymerase structural gene and ORF2. The structural gene and ORF2 could then be recovered on a 2.6 kb BamH1-Xho1 fragment and ligated into BamH1/Sal1 digested pAeTB1 to obtain plasmid pAeP1. The entire insert of pAeP1 containing the phbC promoter -PHA polymerase structural gene—ORF2 construct was then excised as a 3.4 EcoR1-Hind111 fragment and cloned into the polylinker region of the broad host range vector pLAFR3 for conjugation into A. eutrophus strains. To construct pAeP2, the 2.6 kb BamH1-Cla1 fragment from pPOB10 and the 2.5 kb Cla1-XHo1 fragment from pP023, containing ORF3, were ligated with BamH1/Sal1 digested pAeTB1 to obtain pAeP2. Again the phbC—PHA polymerase—ORF2—ORF3 construct could be excised as a 5.9 kb EcoR1—HindIII fragment and cloned into the polylinker region of pLAFR3 to obtain pLAP2. pLAP1 should express both the PHA polymerase and ORF2 in A. eutrophus and pLAP2 should in addition express ORF3. If the genes are not expressed, they can be inserted into the broad host range expression vectors described above for the 8-ketothiolase and NADP-specific acetoacetyl-CoA reductase genes.

The PHB polymerase and PHA polymerase genes should prove invaluable for the production of PHA polymers in bacterial and plant systems. However, the cloned and characterized genes can be further modified by constructing fusions of the two polymerases or by chemical mutagenesis. Functional polymerase enzymes could then be selected in an appropriate organism by the accumulation of polymer detectable by phenotypic appearance or increased density. This is a straightforward approach to altering the enzyme's specificity to create novel polymerases.

Modification of Polymer Synthesis by Varying Levels of Enzyme Expression

After isolation and characterization of the polymer genes and gene products from a variety of organisms, as demonstrated for Z. ramigera, A. eutrophus, N. salmonicolor, and P. oleovarans, a means for controlling the expression of the gene products can be established. Overproduction of the Zoogloea thiolase gene was demonstrated by the studies used to define the transcription start site and promoter of the Z. ramigera. Overproduction enables the purification of the enzymes to homogeneity and provides reagent type quantities for analysis and comparison of substrate specificieties. In addition, the purified enzymes can be used to synthesize stereospecific substrates for in vitro polymer synthesis. Further, once the transcriptional regulatory mechanism responsible for polymer overproduction is elucidated under a variety of environmental conditions, in vitro systems for the enzymatic synthesis of known polymers, and novel polymers, can be developed to provide new materials. The new materials are then analyzed for chemical composition, molecular weight and rheological characteristics so that maximum utilization can be made of the polymers.

An overproduction system for the Z. ramigera thiolase in E. coli was constructed using the synthetic tac promoter to produce a series of thiolase expression plasmids, the optimum construct in induced in E. coli cells yielding about 20–30% of the total soluble cell protein as thiolase. This method yields thiolase in reagent type quantities, an average of 150 mg of pure thiolase from 1 liter of culture.

There are essentially two conditions where gene regulation in Z. ramigera and A. eutrophus may be expected to occur: when carbon starved cells under nutrient limiting conditions are subsequently presented with a carbon source and when cells grown under nutrient limiting conditions have accumulated large amounts of PHB and the nutrient limitation is removed, resulting in PHB degradation.

Transcriptional regulation of the polymer biosynthetic genes is determined as follows. Cultures grown under various conditions are harvested both for enzyme assays (thiolase, reductase and synthetase) and for RNA purification. RNA samples are analyzed in a series of Northern hybridization experiments using the cloned genes as probes. Useful RNA hybridization methodology includes glyoxylation of RNA (McMaster and Carmichael, Proc. Natl. Acad. Sci. USA 74, 4835 (1977)); formaldehyde/agarose gel electrophoresis (Lehrach et al., Proc. Natl. Acad. Sci. USA 16, 4743 (1977)); transfer to nitrocellulose or nylon filters (Thomas, Proc. Nat. Acad. Sci. USA 77, 5201 (1980)); and hybridization with DNA probes labelled with $^{32}P$ by nick translation (Rigby et al., J. Mol. Biol. 113, 237 (1977)). DNA probes are prepared from clones pUCDBK1 (Z. ramigera); and pAeT3 (A. eutrophus). One result of these studies is the establishment of the operon organization of the genes and the length of the mRNA.

The levels of each of the biosynthetic enzymes are manipulated and the effect this has on polymer synthesis monitored. It is necessary to determine the rate-limiting enzyme(s) in the biosynthetic pathway so that one can increase flux through the pathway by overproducing the rate-limiting enzyme(s); the effect overproduction of each enzyme has on the incorporation of different monomeric units, i.e., the ratio of PHB:PHV in the copolymer produced by A. eutrophus when grown on butyrate; and the result of expression of the genes from one species in other species, for example, the expression of Zoogloea genes in A. eutrophus, and vice versa, as well as other isolated and characterized heterologous genes from other organisms, e.g., Nocardia and P. oleovarans in Zoogloea and A. eutrophus.

To accomplish overproduction of polymer biosynthetic genes in multiple host organisms, one must use broad host range expression vectors which function in these bacteria. In one instance, enzyme overproduction via gene dosage is carried out. For example, the entire pUCDBK1 insert containing the promoter region can be cloned into the vector pSUP104 (Simon et al., Molecular Genetics of the Bacteria-Plant Interaction, A. Pobler, ed. (Spring-Verlag, N.Y. 1983) and used to transform Z. ramigera I-16-M. The extent of overproduction of each enzyme is monitored by enzyme assays. A similar approach can be taken for any number of other genes; for example, thiolase; thiolase and reductase; reductase; reductase and synthetase, etc. Secondly, genes can be placed under the transcriptional control of high efficiency promoters, i.e., tac (Gill et al., J. Bact. 167, 611–615 (1986) and tol (Mermod et al., J. Bact. 167, 447–454 (1986). In this case, the constructs are conjugated into mutants defective in the corresponding gene. The expression of the polymer biosynthetic gene or genes of interest can then be tightly regulated, as determined using enzyme assays to monitor the level of overproduction. As each construct is tested, one can begin to monitor the effect on polymer synthesis in a routine manner i.e., the rate and level of synthesis.

Modification of Polymer Synthesis by Altering Available Substrate or Enzyme Specificity.

Factors which determine the molecular weight of the PHB or PHA produced by different bacteria can be eludicated by analysing the molecular weight distribution of the polymers produced by various bacteria. There is little doubt that a number of PHB-producing microorganisms have the ability to incorporate monomers other than D(-)-hydroxybutyrate into the polymer chain. For the PHB-PHV copolymer produced by A. eutrophus, it has been proposed that propionate is first converted to propionyl-CoA which then acts as a substrate for beta-ketothiolase. The high yields of pure enzymes available from overproduction systems is necessary to determine the range of alternate substrate which each of the three PHB-biosynthetic enzymes can utilize and the types of new PHB-like polymers that can be synthesized in an in vitro system where the available substrates can be strictly controlled.

Although the thiolase and reductase enzymes are an essential part of the biosynthesis of PHB and PHB-like polymers, it is the PHB polymerase which ultimately defines the new types of polymer which can be made. This is facilitated by the development of an in vitro system using the enzyme to test a whole range of substrates, many of which cannot enter the cell and therefore cannot be tested for incorporation into PHB by a fermentation process.

Overproduction and purification of more than one reductase enzyme provides a means for comparing the kinetics and specificity of the enzymes. The Zoogloea reductase has been reported to be NADP-specific, however, the A. eutrophus enzyme apparently will use either NAD or NADP. The stereospecificity of this enzyme may make it a useful reagent for the synthesis of D-substrates for PHB polymerase studies. Among the acetoacetyl derivatives to be tested are the oxoester of CoA and oxopantetheine pivaloate (OPP) ad the methylene analogs. The ketone but not the oxoester of the methylene analogs is cleaved by Zoologea thiolase.

Various longer chain alkyl derivatives when R does not equal H, and in particular the $C_5$–$C_8$ linear 3-oxo thiolesters, oxoesters and methylene ketones, may also be useful as substrates for the PHB polymerase, given the existence of $C_5$–$C_8$-beta-hydroxyalkanoates in B. megaterium, as well as olefins, alcohols and epoxides.

In crude extracts of Z. ramigera, D-beta-hydroxybutyryl CoA, but not L-hydroxybutyryl CoA, is a substrate for PHB polymerase. It is expected that other D-hydroxyacyl CoA species can utilize alternate substrates or cosubstrates such as D-beta-hydroxyvaleryl CoA (HV-CoA). [2-$^3$H]HB-CoA and beta[3-$^{24}$C]-HV-CoA, each readily preparable by enzymic or chemical synthesis, can be used as substrates and to monitor $^3$H and $^{14}$C content and ratios in polymers precipitated or separated by gel filtration. It is predicted that block copolymer regions, e.g., $(HB)_{500}(HV)_{1000}(HB)_{500}$, can be constructed by careful control of substrate ratios, and leaving groups in elongation phase, e.g., HB-oxo-CoA and HV-S-CoA monomers.

Additional alternate substrates can be tested including branched chain beta-hydroxyacyl CoAs. Testing cannot be done in whole cells since such compounds are not normally transported into the cells. Alternate substrates can be tested for inhibition of normal [$^{14}$C]-PHB formation first by incorporation of soluble [$^{14}$C]-HBCoA into insoluble polymer, then as copolymerization cosubstrates and finally for homopolymerization. Alternate substrates can be assayed for $K_m$, $V_{max}$ relative to HB-CoA and for polymer size determined by calibrated gel filtration studies.

Method for Production of PHB on a Continuous Basis

PHB is produced and stored in bacteria when they are grown under nutrient limiting conditions, usually nitrogen-limiting conditions (for example, 0.1% nitrogen, depending on the species), although culturing the bacteria under conditions providing limited oxygen, phosphate, or other non-carbon nutrient source will also induce PHB synthesis and storage. For example, Azotobacter beijerinckii, a nitrogen fixing bacteria accumulates up to 70% dry cell weight as PHB when grown on glucose/ammonium salts under limiting oxygen. Increasing the available oxygen leads to a decrease in PHB synthesis and a concomittant reduction in the levels of two of the biosynthetic enzymes. The reduction in enzyme levels is indicative of a regulatory mechanism(s) operating at the genetic level. Nitrogen limitation of the growth of Alcaligenes eutrophus results in yields of up to 80% dry cell weight PHB. Similarly, Halobacterium and Pseudomonas sp. increase PHB production under nitrogen limitation.

Under non-limiting conditions, the PHB in organisms that normally produce the PHB is rapidly degraded by degradative enzymes. It is possible to mutate these organisms such that the degradative enzymes are inactive or deleted, hence PHB accumulated during limiting conditions of growth cannot be degraded under non-limiting conditions. In order for these bacteria to resume growth, the PHB will be excreted into the medium. Alternatively, it is possible to introduce the requisite enzymes into an organism which does not metabolize PHB (biosynthesis or degradation), enabling that organism to accumulate large quantities of PHB under limiting conditions, and when conditions are changed to non-limiting, the organism should release the PHB into the medium.

By cycling the limiting and non-limiting conditions, it is possible to accumulate the maximum amount of PHB (based on absorbance of the bacteria, which increases as a function of polymer content), then release the accumulated polymer into the medium by changing the conditions to non-limiting conditions which stimulate replication of the bacteria. The organisms can be cultured in conventional fermentation systems for continuous removal of the polymer containing medium without disruption of the bacteria.

Expression in Plants and Production of PHB and PHA Polymers

As described above with reference to bacterial expression systems, the genes encoding the thiolase, reductase, and/or the polymerase for PHB or PHA can be expressed in plants of a variety of species to produce the desired polymeric product. The advantages of such a system are immediately apparent, decreasing dependence on petroleum-based plastics, and creating an economically useful crop for plants which can grow on a variety of soils.

The first requirement for plant genetic engineering is a system to deliver the foreign DNA to plant tissue. The most popular vectors at this time are the tumour-inducing (Ti) plasmids of *Agrobacterium tumefaciens*, using this bacterium as the agent to deliver DNA by infection. Plant DNA viruses can also be used as vectors, such as vectors based upon the cauliflower mosaic viruses or the Gemini virus vectors. There are also a number of methods of direct gene transfer to plant cells, including chemically stimulated DNA uptake by protoplasts, electroporation, electroinjection of intact plant cells, liposome-mediated transformation of protoplasts, and DNA transformation by direct injection into plants. Chemically stimulated uptake involves incubating protoplasts with donor and carrier DNA in the presence of 13% (w/v) polyethylene glycol in 40 mM CaCl. Post-incubation is carried out whereby the PEG concentration is gradually lowered as the $CaCl_2$ concentration is gradually raised. Electroporation is the process whereby electrical pulses of high field strength are used to reversibly permeabilize cell membranes to facilitate uptake of large molecules, including DNA. Electroinjection and direct injection have the advantage that they do not require formation of protoplasts first. These methods are known to those skilled in the art. See, for example, the review by C. P. Lichtenstein and S. L. Fuller, "Vectors for the genetic engineering of plants", *Genetic Engineering*, ed. P. W. J. Rigby, vol. 6, 104–171 (Academic Press Ltd. 1987).

The genes can be introduced into the cytoplasm, mitrochondria, or chloroplasts, either directly or using targeting sequences. Vectors and targeting sequences and promoters for plants are known to those skilled in the art and art commercially available from Pharmacia-LKB Biotechnology, 800 Centennial Ave., Piscataway, N.J. 08854-9932, and Stragene, La Jolla, Calif.

Any type of plant which produces a useful carbon substrate can be engineered for polymer production. As used with reference to production of polymers in plants, "polymer" includes PHB, PHA, and novel carbon-based polymers synthesized from fatty acids using the disclosed polymerases. If the plant does not form the appropriate fatty acids, the thiolase and reductase genes can be introduced into the plant along with one or more polymerases. The *A. eutrophus* polymerase polymerizes C4 and C5 substrates. The *P. oleovarans* polymerase acts on longer substrates, such as C6 to C18 fatty acids, but not short chain fatty acids. The plants can also be modified, preferably by mutagenesis, to block the glycerol ester and fatty acid degradation pathways so that the plant forms the appropriate substrate.

The genes can be introduced into any type of plant. Cereal plants are preferred, such as corn, wheat and rice, since they are widely grown and their genetic systems are well characterized. Other useful agronomic plants include tobacco and high oil seed plants, especially those varieties which grow in desert or in mineralized soil.

The genes can also be introduced into plant cell culture systems, many of which are known to those skilled in the art. Cell culture of a variety of cereal and other agricultural crops is described in detail in *Handbook of Plant Cell Culture* vol. 4 edited by D. A. Evans, W. R. Sharp, and P. V. Ammirato (Macmillan Publishing Co. N.Y. 1986). A specific example of a plant system in which much genetic work has been conducted is *Arabidopsis thaliana*. Polymer production in cell culture can be manipulated not only by introduction of the cloned genes but also be variation in substrates and culture conditions, as described with reference to production in bacteria.

Modifications and variations of the present invention, a method for making polyhydroxybutyrate and polyhydroxybutyrate-like polymers having carbon-carbon backbones using recombinant engineering according to the foregoing detailed description, and the resulting polymers, will be obvious to those skilled in the art. Such variations and modifications are intended to come within the scope of the appended claims.

We claim:

1. A method for constructing non-polyhydroxybutyrate polymers and copolymers in a host comprising:
    selecting a host for expression of genes encoding enzymes required for synthesis of non-polyhydroxybutyrate polymers and copolymers,
    introducing into the host isolated genes enzymes selected from the group consisting of beta-ketothiolases, acetoacetyl-CoA reductases, polyhydroxybutyrate polymerases, and polyhydroxyalkanoate polymerases in combination with regulatory sequences for expression of the genes in the host,
    expressing the enzymes encoded by the introduced genes, and
    providing appropriate substrates for the expressed enzymes to synthesize non-polyhydroxybutyrate polymers and copolymers.

2. The method of claim 1 further comprising selecting the enzymes on the basis of their substrate specificity.

3. The method of claim 1 further comprising altering the substrate specifically of the enzymes by modifying the genes encoding the enzymes.

4. The method of claim 1 further comprising providing regulatory sequences in the expression vector which control expression of the genes encoding the enzymes requires for synthesis of non-polyhydroxybutyrate polymers and copolymers in response to specific inducers.

5. The method of claim 4 wherein the inducer is selected from the group consisting of temperature changes and specific substrate.

6. The method of claim 1 wherein the genes are from bacteria selected from the group consisting of *Zoogloea, Azotobacter, Alcaligenes, Bacillus, Nocardia, Clostridium, Halobacterium, Escherichia, Pseudomonas* and *Rhodospirillium*.

7. The method of claim 1 further comprising expressing the genes in bacterial hosts which are deficient in at least one enzymes required for synthesis of non-polyhydroxybutyrate polymers and copolymers.

8. The method of claim 1 further comprising expressing the genes in plant hosts.

9. The method of claim 1 wherein the genes encode enzymes stereospecific for the D isomer of the Hydroxyacyl CoA substrate.

10. The biopolymer produced by the method of claim 1.

11. A system for synthesizing biopolymers having polyester backbones comprising:

selecting a host for expression of genes encoding enzymes required for synthesis of polyhydroxyalkanoates, introducing into the host isolated structural genes encoding enzymes selected from the group consisting of beta-ketothiolases, acetoacetyl-CoA reductases, polyhydroxybutyrate polymerases, and polyhydroxyalkanoate polymerases in combination with regulatory sequences for expression of the genes in the host, and providing appropriate substrates for the enzymes to synthesis polyhydroxyalkanoates.

12. The system of claim 11 wherein the host is selected from the group consisting of bacteria and plants.

13. A method for constructing polyhydroxybutyrate copolymers in a host comprising:

selecting a host for expression of genes encoding enzymes required for synthesis of polyhydroxybutyrate copolymers, introducing into the host isolated structural genes encoding enzymes selected from the group consisting of beta-ketothiolases, acetoacetyl-CoA reductases, polyhydroxybutyrate polymerases, and polyhydroxyalkanoate polymerases in combination with regulatory sequences for expression of the gene in the host, expressing the enzymes encoded by the introduced genes, and providing appropriate substrates for the expressed enzymes to synthesize polyhydroxybutyrate copolymers.

* * * * *

UNITED STATES PATENT AND TRADEMARK OFFICE
CERTIFICATE OF CORRECTION

PATENT NO. : 6,881,560 B2
DATED : April 19, 2005
INVENTOR(S) : Oliver P. Peoples et al.

It is certified that error appears in the above-identified patent and that said Letters Patent is hereby corrected as shown below:

Title page,
Item [63], Related U.S. Appliciation Data, please delete ", which is a continuation-in-part of application No. 07/067,695, filed on Jun. 29, 1987, now abandoned".

Column 26,
Line 30, delete "isolated genes" and replace it with -- isolated structural genes encoding --.
Line 44, delete "specifically" and replace it with -- specificity --.
Line 48, delete "requires" and replace it with -- required --.
Line 61, delete "enzymes" and replace it with -- enzyme --.

Signed and Sealed this

Twenty-third Day of August, 2005

JON W. DUDAS
*Director of the United States Patent and Trademark Office*